United States Patent
Bogen et al.

(10) Patent No.: US 12,331,018 B2
(45) Date of Patent: *Jun. 17, 2025

(54) PYRROLIDINE OREXIN RECEPTOR AGONISTS

(71) Applicant: Merck Sharp & Dohme LLC, Rahway, NJ (US)

(72) Inventors: Stephane L. Bogen, Somerset, NJ (US); Michael J. Breslin, Drexel Hill, PA (US); Dane James Clausen, Rahway, NJ (US); Anthony Ginnetti, Perkasie, PA (US); Michael T. Rudd, Collegeville, PA (US); Shawn J. Stachel, Perkasie, PA (US); Craig A. Stump, Pottstown, PA (US); Dexi Yang, Livingston, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 898 days.

This patent is subject to a terminal disclaimer.

(21) Appl. No.: 17/430,409

(22) PCT Filed: Feb. 11, 2020

(86) PCT No.: PCT/US2020/017573
§ 371 (c)(1),
(2) Date: Aug. 12, 2021

(87) PCT Pub. No.: WO2020/167701
PCT Pub. Date: Aug. 20, 2020

(65) Prior Publication Data
US 2022/0144771 A1    May 12, 2022

Related U.S. Application Data

(60) Provisional application No. 62/804,995, filed on Feb. 13, 2019.

(51) Int. Cl.
*C07D 207/14* (2006.01)

(52) U.S. Cl.
CPC .................................. *C07D 207/14* (2013.01)

(58) Field of Classification Search
CPC .................................................. C07D 207/14
See application file for complete search history.

(56) References Cited

U.S. PATENT DOCUMENTS

| | | |
|---|---|---|
| 9,527,807 B2 | 12/2016 | Fukumoto et al. |
| 2017/0226137 A1 | 8/2017 | Fujimoto et al. |
| 2020/0385346 A1* | 12/2020 | Fujimoto ............ A61P 25/28 |

FOREIGN PATENT DOCUMENTS

| | | |
|---|---|---|
| EP | 3594202 A1 | 1/2020 |
| EP | 3594203 A1 | 1/2020 |
| EP | 3663281 A1 | 6/2020 |
| WO | 2012137982 A2 | 10/2012 |
| WO | 2017135306 A1 | 8/2017 |
| WO | 2018164191 A1 | 9/2018 |
| WO | 2018164192 A1 | 9/2018 |
| WO | 2019027003 A1 | 2/2019 |
| WO | 2019027058 A1 | 2/2019 |
| WO | 2019089991 A1 | 5/2019 |
| WO | 2020167706 A1 | 8/2020 |

OTHER PUBLICATIONS

Chemelli, Richard M. et al., Narcolepsy in orexin Knockout Mice: Molecular Genetics of Sleep Regulation, Cell, 1999, 437-451, 98.
Harris, Glenda C. et al., Arousal and reward: a dichotomy in orexin function, Trends in Neurosciences, 2006, 571-577, 29(10).
Peyron, Christelle et al., Neurons Containing Hypocretin (Orexin) Project to Multiple Neuronal Systems, The Journal of Neuroscience, 1998, 9996-100150, 18(23).
Sakurai, Takeshi et al., Orexins and Orexin Receptors: A Family of Hypothalamic Neuropeptides and G Protein-Coupled Receptors that Regulate Feeding Behavior, Cell, 1998, 573-585, 92.
Extended European Search Report for 20755082.3, mailed Jul. 14, 2022; 7 pages.

\* cited by examiner

*Primary Examiner* — Bong-Sook Baek
(74) *Attorney, Agent, or Firm* — Dianne Pecoraro; John C. Todaro

(57) ABSTRACT

The present invention is directed to pyrrolidine compounds which are agonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

6 Claims, No Drawings

PYRROLIDINE OREXIN RECEPTOR AGONISTS

CROSS REFERENCE TO RELATED APPLICATIONS

The present application is the 371 national phase application of International Application No. PCT/US2020/017573, filed Feb. 11, 2020, which claims the benefit of U.S. Provisional Application No. 62/804,995, filed Feb. 13, 2019, hereby incorporated by reference in their entirety.

BACKGROUND OF THE INVENTION

The orexins (hypocretins) comprise two neuropeptides produced in the hypothalamus: orexin A (OX-A) (a 33 amino acid peptide) and the orexin B (OX-B) (a 28 amino acid peptide) (Sakurai T. et al., Cell, 1998, 92, 573-585). Orexins regulate states of sleep and wakefulness opening potentially novel therapeutic approaches for narcolepsy, idiopathic hypersomnia, excessive daytime sleepiness, shift work disorder, obstructive sleep apnea and insomnia (Chemelli R. M. et al., Cell, 1999, 98, 437-451). Orexins are found to stimulate food consumption in rats suggesting a physiological role for these peptides as mediators in the central feedback mechanism that regulates feeding behavior (Sakurai T. et al., Cell, 1998, 92, 573-585). Orexins have also been indicated as playing a role in arousal, emotion, energy homeostasis, reward, learning and memory (Peyron, et al., Journal Neurosci., 1998,18(23):9996-100150, Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is partially selective for OX-A and the orexin-2 receptor (OX2 or OX2R) is capable of binding OX-A as well as OX-B with similar affinity. The physiological actions in which orexins are presumed to participate are thought to be expressed via one or both of OX1 receptor and OX2 receptor as the two subtypes of orexin receptors.

SUMMARY OF THE INVENTION

The present invention is directed to pyrrolidine compounds which are agonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

DETAILED DESCRIPTION OF THE INVENTION

The present invention is directed to compounds of the formula I:

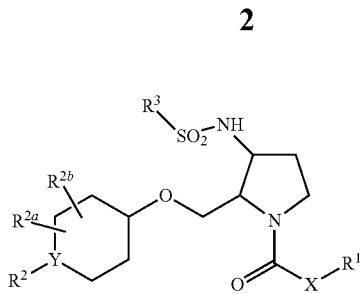

wherein:
X is —O— or —NH—, or X may be a direct bond to $R^1$;
Y is N or CH;
$R^1$ is selected from:
  (1) —$C_{1-6}$alkyl, where the alkyl is unsubstituted or substituted with one to six substituents independently selected from $R^4$, and
  (2) —$C_{3-6}$cycloalkyl, where the cycloalkyl is unsubstituted or substituted with one to six substituents independently selected from $R^4$;
$R^2$ is selected from:
  (1) hydrogen,
  (2) —$C_{1-6}$alkyl, where the alkyl is unsubstituted or substituted with one to six substituents independently selected from $R^4$,
  (3) —$C_{3-6}$cycloalkyl, where the cycloalkyl is unsubstituted or substituted with one to six substituents independently selected from $R^4$,
  (4) -phenyl, where the phenyl is unsubstituted or substituted with one to three substituents independently selected from $R^4$, and
  (5) -heteroaryl, where the heteroaryl is selected from: pyridyl, pyrimidinyl, and pyrazinyl, and the heteroaryl is unsubstituted or substituted with one to three substituents independently selected from $R^4$;
$R^{2a}$ and $R^{2b}$ are independently selected from:
  (1) hydrogen,
  (2) hydroxyl,
  (3) halogen, and
  (4) —$C_{1-6}$alkyl, where the alkyl is unsubstituted or substituted with one to six substituents independently selected from halogen;
$R^3$ is selected from:
  (1) —$C_{1-6}$alkyl, where the alkyl is unsubstituted or substituted with one to six substituents independently selected from $R^4$,
  (2) —$C_{3-6}$cycloalkyl, where the cycloalkyl is unsubstituted or substituted with one to six substituents independently selected from $R^4$,
  (3) -phenyl, where the phenyl is unsubstituted or substituted with one to three substituents independently selected from $R^4$,
  (4) —$NR^{10}R^{11}$; wherein $R^{10}$ and $R^{11}$ are independently selected from:
    (a) hydrogen, and
    (b) $C_{1-6}$alkyl, which is unsubstituted or substituted with one to six $R^4$;
$R^4$ is selected from:
  (1) hydroxyl,
  (2) halogen,
  (3) $C_{1-6}$alkyl, which is unsubstituted or substituted with one to six fluoro,
  (4) —$C_{3-6}$cycloalkyl,
  (5) —O—$C_{1-6}$alkyl,
  (6) —O(C=O)—$C_{1-6}$alkyl,
  (7) —$NH_2$, (8) —NH—C$_{1-6}$alkyl,
(9) —NO$_2$,
(10) phenyl,
(11) —CO$_2$H, and
(12) —CN;
or a pharmaceutically acceptable salt thereof.

An embodiment of the present invention includes compounds of the formula Ia:

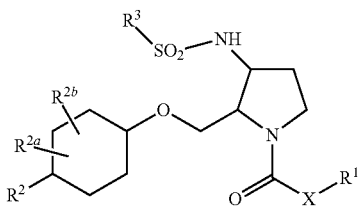

Ia wherein X, R$^1$, R$^2$, R$^{2a}$, R$^{2b}$, and R$^3$ are defined herein; or a pharmaceutically acceptable salt thereof.

An embodiment of the present invention includes compounds of the formula Ib:

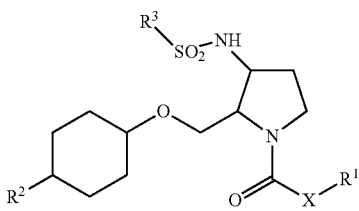

Ib wherein X, R$^1$, R$^2$, and R$^3$ are defined herein; or a pharmaceutically acceptable salt thereof.

An embodiment of the present invention includes compounds of the formula Ib':

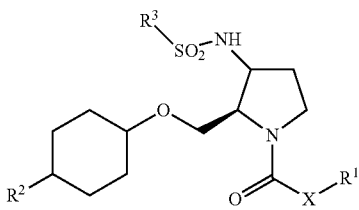

Ib' wherein X, R$^1$, R$^2$, and R$^3$ are defined herein; or a pharmaceutically acceptable salt thereof.

An embodiment of the present invention includes compounds of the formula Ib":

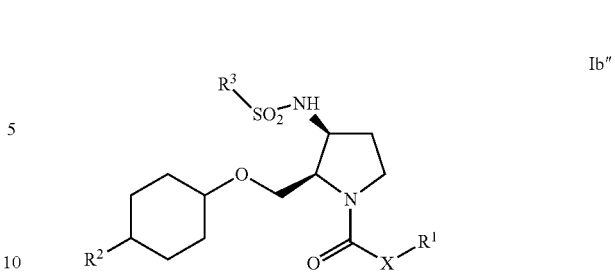

Ib"

wherein X, R$^1$, R$^2$, and R$^3$ are defined herein; or a pharmaceutically acceptable salt thereof.

An embodiment of the present invention includes compounds of the formula Ic:

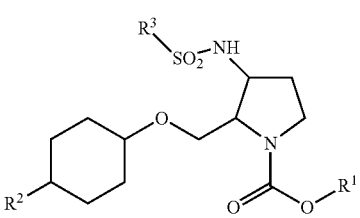

Ic wherein R$^1$, R$^2$, and R$^3$ are defined herein; or a pharmaceutically acceptable salt thereof.

An embodiment of the present invention includes compounds of the formula Ib':

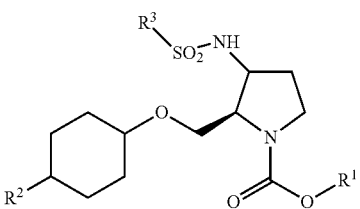

Ic' wherein R$^1$, R$^2$, and R$^3$ are defined herein; or a pharmaceutically acceptable salt thereof.

An embodiment of the present invention includes compounds of the formula Ic":

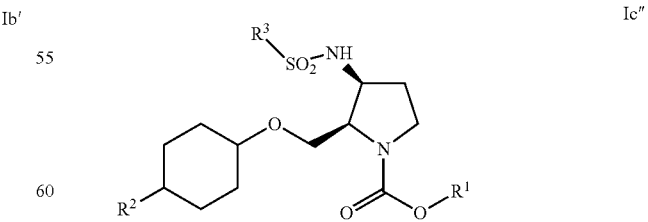

Ic"

wherein R$^1$, R$^2$, and R$^3$ are defined herein; or a pharmaceutically acceptable salt thereof.

An embodiment of the present invention includes compounds of the formula Id:

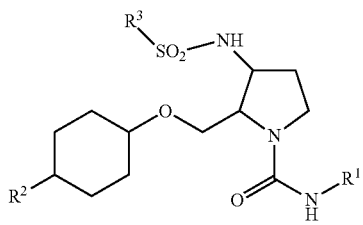

Id wherein $R^1$, $R^2$, and $R^3$ are defined herein; or a pharmaceutically acceptable salt thereof.

An embodiment of the present invention includes compounds of the formula Id':

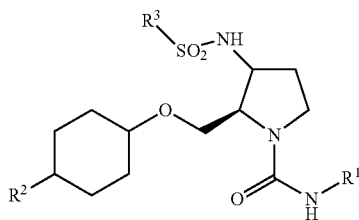

Id' wherein $R^1$, $R^2$, and $R^3$ are defined herein; or a pharmaceutically acceptable salt thereof.

An embodiment of the present invention includes compounds of the formula Id":

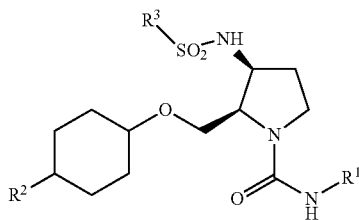

Id"

wherein $R^1$, $R^2$, and $R^3$ are defined herein; or a pharmaceutically acceptable salt thereof.

An embodiment of the present invention includes compounds of the formula Ie:

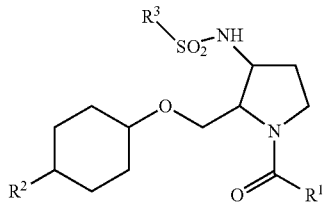

Ie wherein $R^1$, $R^2$ and $R^3$ are defined herein; or a pharmaceutically acceptable salt thereof.

An embodiment of the present invention includes compounds of the formula Ie':

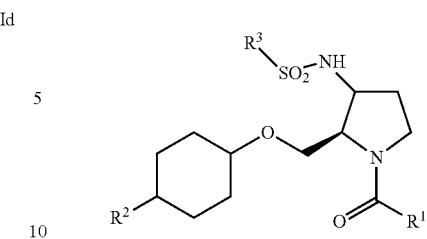

Ie' wherein $R^1$, $R^2$ and $R^3$ are defined herein; or a pharmaceutically acceptable salt thereof.

An embodiment of the present invention includes compounds of the formula Ie":

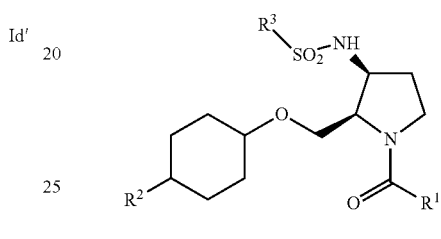

Ie"

wherein $R^1$, $R^2$ and $R^3$ are defined herein; or a pharmaceutically acceptable salt thereof.

An embodiment of the present invention includes compounds wherein X is —O—.

An embodiment of the present invention includes compounds wherein X is —NH—. An embodiment of the present invention includes compounds wherein X is a direct bond to $R^1$.

An embodiment of the present invention includes compounds wherein Y is N. An embodiment of the present invention includes compounds wherein Y is CH.

An embodiment of the present invention includes compounds wherein $R^1$ is selected from:
 (1) —$C_{1-6}$ alkyl, which is unsubstituted or substituted with fluoro or —O(C=O)—$C_{1-6}$alkyl,
 (2) —$C_{3-6}$cycloalkyl, and
 (3) —$CH_2$—$C_{3-6}$cycloalkyl.

An embodiment of the present invention includes compounds wherein $R^1$ is selected from:
 (1) methyl,
 (2) ethyl,
 (3) —$CH_2OH$,
 (4) —$CH_2CF_3$,
 (5) —$CH_2CHF_2$,
 (6) —$CH(CH_3)_2$,
 (7) —$CH_2CH_2CH_2F$,
 (8) cyclopropyl,
 (9) —$CH_2$-cyclopropyl,
 (10) —$CH_2$-cyclobutyl, and
 (11) —$CH_2O(C=O)CH_3$.

An embodiment of the present invention includes compounds wherein $R^2$ is selected from:
 (1) hydrogen,
 (2) —$C_{1-6}$alkyl, where the alkyl is unsubstituted or substituted with one to three fluoro, and
 (3) phenyl, which is unsubstituted or substituted with —$C_{1-6}$alkyl, where the alkyl is unsubstituted or substituted with one to three fluoro.

An embodiment of the present invention includes compounds wherein $R^2$ is selected from:

(1) hydrogen,
(2) —CH$_2$(CH$_3$)$_2$,
(3) —CF$_3$,
(4) —CH$_2$CHF$_2$,
(5) —CH$_2$CF$_3$, and
(6) phenyl, which is unsubstituted or substituted with —CF$_3$ or —CH$_2$CF$_3$.

An embodiment of the present invention includes compounds wherein R$^{2a}$ is hydrogen and R$^{2b}$ is hydrogen. An embodiment of the present invention includes compounds wherein R$^{2a}$ is methyl and R$^{2b}$ is hydrogen. An embodiment of the present invention includes compounds wherein R$^{2a}$ is methyl and R$^{2b}$ is methyl. An embodiment of the present invention includes compounds wherein R$^{2a}$ is methyl and R$^{2b}$ is methyl, wherein R$^{2a}$ and R$^{2b}$ are attached to the same carbon atom. An embodiment of the present invention includes compounds wherein R$^{2a}$ is fluoro and R$^{2b}$ is fluoro, wherein R$^{2a}$ and R$^{2b}$ are attached to the same carbon atom.

An embodiment of the present invention includes compounds wherein R$^3$ is selected from:
(1) —C$_{1-6}$alkyl, where the alkyl is unsubstituted or substituted with one to three fluoro,
(2) —C$_{3-6}$cycloalkyl,
(3) —NH$_2$,
(4) —NH(C$_{1-6}$alkyl),
(5) —N(C$_{1-6}$alkyl)(C$_{1-6}$alkyl), and
(6) -phenyl.

An embodiment of the present invention includes compounds wherein R$^3$ is selected from:
(1) methyl,
(2) —CF$_3$,
(3) —CH$_2$F,
(4) ethyl,
(5) cyclopropyl,
(6) —CH(CH$_3$)$_2$,
(7) —NH(CH$_3$),
(8) —N(CH$_3$)$_2$, and
(9) -phenyl.

Certain embodiments of the present invention include a compound which is selected from the group consisting of the subject compounds of the Examples herein or a pharmaceutically acceptable salt thereof.

Certain embodiments of the present invention include a compound which is selected from:

N-ethyl-3-(methylsulfonamido)-2-(((4-phenylcyclohexyl)oxy)methyl)pyrrolidine-1-carboxamide; (CIS)-N-ethyl-3-(methylsulfonamido)-2-((((CIS)-4-phenylcyclohexyl)oxy)methyl)pyrrolidine-1-carboxamide;
methyl 3-(methylsulfonamido)-2-(((4-phenylcyclohexyl)oxy)methyl)pyrrolidine-1-carboxylate; methyl (CIS)-3-(methylsulfonamido)-2-((((CIS)-4-phenylcyclohexyl)oxy)methyl)pyrrolidine-1-carboxylate;
N-(1-acetyl-2-(((4-phenylcyclohexyl)oxy)methyl)pyrrolidin-3-yl)methanesulfonamide;
N-((CIS)-1-acetyl-2-((((CIS)-4-phenylcyclohexyl)oxy)methyl)pyrrolidin-3-yl)methanesulfonamide;
ethyl 3-(methylsulfonamido)-2-(((4-phenylcyclohexyl)oxy)methyl)pyrrolidine-1-carboxylate; ethyl (CIS)-3-(methylsulfonamido)-2-((((CIS)-4-phenylcyclohexyl)oxy)methyl)pyrrolidine-1-carboxylate;
isopropyl 3-(methylsulfonamido)-2-(((4-phenylcyclohexyl)oxy)methyl)pyrrolidine-1-carboxylate; isopropyl (CIS)-3-(methylsulfonamido)-2-((((CIS)-4-phenylcyclohexyl)oxy)methyl)pyrrolidine-1-carboxylate;
2-fluoroethyl 3-(methylsulfonamido)-2-(((4-phenylcyclohexyl)oxy)methyl)-pyrrolidine-1-carboxylate;
2-fluoroethyl (CIS)-3-(methylsulfonamido)-2-((((CIS)-4-phenylcyclohexyl)oxy)methyl)-pyrrolidine-1-carboxylate;
2-(3-(methylsulfonamido)-2-(((4-phenylcyclohexyl)oxy)methyl)pyrrolidin-1-yl)-2-oxoethyl acetate;
2-((CIS)-3-(methylsulfonamido)-2-((((CIS)-4-phenylcyclohexyl)oxy)methyl)pyrrolidin-1-yl)-2-oxoethyl acetate;
N-(1-(cyclopropanecarbonyl)-2-(((4-phenylcyclohexyl)oxy)methyl)pyrrolidin-3-yl)methanesulfonamide;
N-((CIS)-1-(cyclopropanecarbonyl)-2-((((CIS)-4-phenylcyclohexyl)oxy)methyl)pyrrolidin-3-yl)methanesulfonamide;
N-isopropyl-3-(methylsulfonamido)-2-(((4-phenylcyclohexyl)oxy)methyl)pyrrolidine-1-carboxamide;
(CIS)-N-isopropyl-3-(methyl sulfonamido)-2-((((CIS)-4-phenylcyclohexyl)oxy)methyl)pyrrolidine-1-carboxamide;
3-(methylsulfonamido)-2-(((4-phenylcyclohexyl)oxy)methyl)-N-(2,2,2-trifluoroethyl)pyrrolidine-1-carboxamide;
(CIS)-3-(methylsulfonamido)-2-((((CIS)-4-phenylcyclohexyl)oxy)methyl)-N-(2,2,2-trifluoroethyl)pyrrolidine-1-carboxamide;
methyl 3-(methylsulfonamido)-2-(((4-phenylcyclohexyl)oxy)methyl)pyrrolidine-1-carboxylate; methyl (2R,3S)-3-(methylsulfonamido)-2-((((CIS)-4-phenylcyclohexyl)oxy)methyl)pyrrolidine-1-carboxylate;
2,2-difluoroethyl 3-(methylsulfonamido)-2-(((4-phenylcyclohexyl)oxy)-methyl)pyrrolidine-1-carboxylate;
2,2-difluoroethyl (2R,3S)-3-(methylsulfonamido)-2-((((CIS)-4-phenylcyclohexyl)oxy)-methyl)pyrrolidine-1-carboxylate;
methyl 3-(ethylsulfonamido)-2-(((4-phenylcyclohexyl)oxy)methyl)pyrrolidine-1-carboxylate; methyl (CIS)-3-(ethylsulfonamido)-2-((((CIS)-4-phenylcyclohexyl)oxy)methyl)pyrrolidine-1-carboxylate;
methyl 3-((1-methylethyl)sulfonamido)-2-(((4-phenylcyclohexyl)oxy)methyl)-pyrrolidine-1-carboxylate;
methyl 3-((1-methylethyl)sulfonamido)-2-(((4-phenylcyclohexyl)oxy)methyl)-pyrrolidine-1-carboxylate;
methyl (CIS)-3-((1-methylethyl)sulfonamido)-2-((((CIS)-4-phenylcyclohexyl)oxy)methyl)-pyrrolidine-1-carboxylate;
methyl 3-(cyclopropanesulfonamido)-2-(((4-phenylcyclohexyl)oxy)methyl)-pyrrolidine-1-carboxylate;
methyl (CIS)-3-(cyclopropanesulfonamido)-2-((((CIS)-4-phenylcyclohexyl)oxy)methyl)-pyrrolidine-1-carboxylate;
methyl 3-((fluoromethyl)sulfonamido)-2-(((4-phenylcyclohexyl)oxy)methyl)-pyrrolidine-1-carboxylate;
methyl (CIS)-3-((fluoromethyl)sulfonamido)-2-((((CIS)-4-phenylcyclohexyl)oxy)methyl)-pyrrolidine-1-carboxylate;
methyl 2-(((4-phenylcyclohexyl)oxy)methyl)-3-(phenylsulfonamido)pyrrolidine-1-carboxylate;
methyl (CIS)-2-((((CIS)-4-phenylcyclohexyl)oxy)methyl)-3-(phenyl sulfonamido)pyrrolidine-1-carboxylate;
methyl 3-((N-methylsulfamoyl)amino)-2-(((4-phenylcyclohexyl)oxy)methyl)-pyrrolidine-1-carboxylate;
methyl (CIS)-3-((N-methylsulfamoyl)amino)-2-((((CIS)-4-phenylcyclohexyl)oxy)methyl)-pyrrolidine-1-carboxylate;
methyl 3-((N,N-dimethylsulfamoyl)amino)-2-(((4-phenylcyclohexyl)oxy)methyl)-pyrrolidine-1-carboxylate;

methyl (CIS)-3-((N,N-dimethylsulfamoyl)amino)-2-((((CIS)-4-phenylcyclohexyl)oxy)methyl)-pyrrolidine-1-carboxylate;
N-(2-(((4-phenylcyclohexyl)oxy)methyl)-1-(3,3,3-trifluoropropanoyl)pyrrolidin-3-yl)methanesulfonamide;
N-((CIS)-2-((((CIS)-4-phenylcyclohexyl)oxy)methyl)-1-(3,3,3-trifluoropropanoyl)pyrrolidin-3-yl)methanesulfonamide;
N-(cyclobutylmethyl)-3-(methylsulfonamido)-2-(((4-phenylcyclohexyl)oxy)methyl)-pyrrolidine-1-carboxamide;
(CIS)-N-(cyclobutylmethyl)-3-(methyl sulfonamido)-2-((((CIS)-4-phenylcyclohexyl)oxy)methyl)-pyrrolidine-1-carboxamide;
N-cyclopropyl-3-(methylsulfonamido)-2-(((4-phenylcyclohexyl)oxy)methyl)-pyrrolidine-1-carboxamide;
(CIS)-N-cyclopropyl-3-(methylsulfonamido)-2-((((CIS)-4-phenylcyclohexyl)oxy)methyl)-pyrrolidine-1-carboxamide;
2,2-difluoroethyl 3-(methylsulfonamido)-2-(((4-phenylcyclohexyl)oxy)methyl)-pyrrolidine-1-carboxylate;
2,2-difluoroethyl (CIS)-3-(methylsulfonamido)-2-((((CIS)-4-phenylcyclohexyl)oxy)methyl)-pyrrolidine-1-carboxylate;
2,2,2-trifluoroethyl 3-(methylsulfonamido)-2-(((4-phenylcyclohexyl)oxy)methyl)-pyrrolidine-1-carboxylate;
2,2,2-trifluoroethyl (CIS)-3-(methylsulfonamido)-2-((((CIS)-4-phenylcyclohexyl)oxy)methyl)-pyrrolidine-1-carboxylate;
N-(1-(2-hydroxyacetyl)-2-(((4-phenylcyclohexyl)oxy)methyl)pyrrolidin-3-yl)methanesulfonamide;
N-((CIS)-1-(2-hydroxyacetyl)-2-((((CIS)-4-phenylcyclohexyl)oxy)methyl)pyrrolidin-3-yl)methanesulfonamide;
N-(1-(cyclopropanecarbonyl)-2-(((4-phenylcyclohexyl)oxy)methyl)pyrrolidin-3-yl)methanesulfonamide;
N-((2S,3R)-1-(cyclopropanecarbonyl)-2-((((CIS)-4-phenylcyclohexyl)oxy)methyl)pyrrolidin-3-yl)methanesulfonamide;
N-(1-(cyclopropanecarbonyl)-2-(((4-phenylcyclohexyl)oxy)methyl)pyrrolidin-3-yl)methanesulfonamide;
N-((2R,3S)-1-(cyclopropanecarbonyl)-2-((((CIS)-4-phenylcyclohexyl)oxy)methyl)pyrrolidin-3-yl)methanesulfonamide;
N-ethyl-2-(((4-isopropylcyclohexyl)oxy)methyl)-3-(methyl sulfonamido)pyrrolidine-1-carboxamide;
(2R,3S)—N-ethyl-2-(((4-isopropylcyclohexyl)oxy)methyl)-3-(methylsulfonamido)pyrrolidine-1-carboxamide;
methyl 2-(((4-isopropylcyclohexyl)oxy)methyl)-3-(methylsulfonamido)pyrrolidine-1-carboxylate;
methyl (2R,3S)-2-(((4-isopropylcyclohexyl)oxy)methyl)-3-(methylsulfonamido)pyrrolidine-1-carboxylate;
N-(1-(cyclopropanecarbonyl)-2-(((4-isopropylcyclohexyl)oxy)methyl)pyrrolidin-3-yl)methanesulfonamide; and
N-((2R,3S)-1-(cyclopropanecarbonyl)-2-(((4-isopropyl cyclohexyl)oxy)methyl)pyrrolidin-3-yl)methanesulfonamide;
or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes suitable for inclusion in the compounds of the invention include isotopes of hydrogen such as $^{2}H$ and $^{3}H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies.

The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

The present invention is also directed to the use of the compounds disclosed herein as agonists of orexin receptor activity. The subject compounds and pharmaceutically acceptable salts thereof are useful in a method of agonizing orexin receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for agonizing orexin receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to agonize the orexin receptor in the subject. In an embodiment, the amount of compound can be an "effective amount", wherein the subject compound is administered in an amount that will elicit the biological or medical response of a tissue, system, animal or human that is being sought by the researcher, veterinarian, medical doctor or other clinician. An effective amount does not necessarily include considerations of toxicity and safety related to the administration of the compound. It is recognized that one skilled in the art may affect neurological and psychiatric disorders associated with orexin receptor activation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and or "administering a" compound should be understood to mean providing a compound of the invention or a prodrug of a compound of the invention to to the subject.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R agonists may be readily determined without undue experimentation by methodology well known in the art. Both the OX1R and/or OX2R G-coupled protein receptors (GPCRs) couple through the Gaq signaling pathway, which ultimately promotes calcium mobilization via inositol triphosphate (IP3) production. The half-life of IP-3 is relatively short, being rapidly metabolized to inositol monophosphate (IP-1), which can be readily detected using a commercially available assay kit (IP-One; Cisbio; cat #621PAPEC) coupled with a cell line expressing the target receptor(s) of interest. The utility of the compounds in accordance with the present invention as orexin receptor OX1R and/or OX2R agonists may be determined utilizing this assay.

In a typical experiment, the OX1 and OX2 receptor agonist activity is determined in accordance with the following general experimental method. Chinese hamster ovary (CHO) cells expressing human OX1R and/or the human OX2R were grown in Iscove's modified DMEM containing glutaMAX™, 1% G418, 100 U/mL penicillin, 100 µg/mL streptomycin and 10% heat-inactivated qualified fetal bovine serum (FBS). The OX2R cells were seeded at 10,000 cells/well/50 µL and the OX1R cells were seeded at 20,000 cells/well/50 µL into 384-well white tissue culture plates (Greiner; cat #781080). All cell/media reagents were from GIBCO-Invitrogen Corp. The seeded cell plate(s) were incubated at 37° C. with 5% $CO_2$ and 85% humidity for 20-24 hours. On the day of the assay, assay-ready compound plates were prepared using an acoustic liquid handler (ECHO; Labcyte), which dispensed sufficient volume of test compound stock (10 mM in DMSO) or 100% DMSO to prepare 10 point, ½-log dilutions in a final volume of 202.5 nL/well in all test wells of a 384-well diamond plate (Labcyte). Following completion of assay-ready plates, importantly, the next three steps were performed with minimal delay: 1) 20 µl of 1× stimulation buffer was added to the compound plate using a Multidrop Combi (small cassette, Thermo Fisher Scientific cat #24073290); 2) culture medium was removed from the cell plate using the Bluewasher plate washer (gentle spin; BlueCatBio); 3) 14 µl of compound/stimulation buffer mixture was added to the cell plate using a Bravo liquid handler (Agilent) prior to incubating cell plates at 37° C. with 5% $CO_2$ and 85% humidity for 1 or 2 hours (OX1R and OX2R, respectively). During this incubation, IP-one detection reagents were prepared (38:1:1 lysis buffer:D2:AB-cryptate reagents). Six µL of mixed detection reagents were added to the cell plate using a Multidrop Combi (small cassette, Thermo Fisher Scientific cat #24073290) and incubated 60 minutes at room temperature in the dark. Fluorescence signal was detected using an Envision plate reader (Perkin Elmer) [LANCE/DELFIA Dual Enh (Em: APC 665; Ex: Cy5 620)].

For each compound, data were fit to a four parameter logistic fit (ActivityBase software) and the $EC_{50}$ was reported as the inflection point of the resulting curve. Percent effect for each test compound was determined as the percentage of sample raw value/mean max effect, where the mean max effect was derived from the mean raw value of 32 control wells per assay plate (using Orexin A (cat #003-30) at 1 µM for human OX1R and a reference compound at 1 uM with 100% activity previously established by comparison to Orexin A for human OX2R). The intrinsic orexin receptor agonist activity of a compound which may be used in the present invention may be determined by these assays.

All of the final compounds of the following examples had activity in agonizing the human orexin-2 receptor in the aforementioned IPOne assay with an $EC_{50}$ of about 0.01 nM to 5000 nM. Additional data is provided in the following Examples. Such a result is indicative of the intrinsic activity of the compounds in use as agonists of orexin-1 receptor and/or the orexin-2 receptor. In general, one of ordinary skill in the art would appreciate that a substance is considered to effectively agonize the orexin receptor if it has an $EC_{50}$ in the IPOne assay of less than about 50 µM, or more specifically less than about 1000 nM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of disorders associated with orexin receptors, including one or more of the following conditions or diseases: narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, wakefulness, nocturnal myoclonus, disturbances of consciousness, such as coma, REM sleep interruptions, jet-lag, excessive daytime sleepiness, shift workers' sleep disturbances, dyssomnias, sleep disorders, sleep disturbances, hypersomnia associated with depression, emotional/mood disorders, Alzheimer's disease or cognitive impairment, Parkinson's disease, Guillain-Barre syndrome, Kleine Levin syndrome, and sleep disorders which accompany aging; Alzheimer's sundowning; conditions associated with circadian rhythmicity as well as mental and physical disorders associated with travel across time zones and with rotating shift-work schedules; fibromyalgia; cardiac failure; diseases related to bone loss; sepsis; syndromes which are manifested by non-restorative sleep and muscle pain or sleep apnea which is associated with respiratory disturbances during sleep; conditions which result from a diminished quality of sleep; and other diseases related to general orexin system dysfunction.

Thus, in certain embodiments the present invention may provide methods for: treating or controlling narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, disturbances of consciousness, REM sleep interruptions, jet-lag, shift workers' sleep disturbances, dyssomnias, night terror, insomnias associated with depression, emotional/mood disorders, Alzheimer's disease or cognitive impairment; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling insulin resistance syndrome; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling Guillain-Barre syndrome; treating or controlling Klein Levin syndrome; treating or controlling psychosis; treating or controlling dysthymic, mood, psychotic and anxiety disorders; treating side effects or complications due to anesthesia; reversal of anesthesia; reversal of anesthesia following surgery; treating or controlling depression, including major depression and major depression disorder; treating or controlling bipolar disorder; or treating, controlling, ameliorating or reducing the risk of schizophrenia, in a mammalian subject which comprises administering to the subject a compound of the present invention.

The compounds of the present invention may also potentially have utility in treating, preventing, ameliorating, controlling or reducing the risk of a variety of other disorders associated with orexin receptors, including one or more of the following conditions or diseases including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia; night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; treating or controlling Guillain-Barre syndrome; treating or controlling Klein Levin syndrome; treating or controlling psychosis; treating or controlling dysthymic, mood, psychotic and anxiety disorders; treating complications due to anesthesia; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize.

Generally, dosage levels of between 0.0001 to 100 mg/kg. of body weight daily are administered to the subject, e.g., humans, adolescent humans and elderly humans, to obtain effective agonism of orexin receptors. The dosage range will generally be about 0.5 mg to 10.0 g. per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered once or multiple times during the day. The compounds may be administered upon awakening or otherwise in the morning, or during waking hours. For example, the compounds may be administered about 1 hour after awakening, about 30 minutes after awakening or immediately after awakening.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with compounds which are known in the art to be useful for treating or controlling narcolepsy, including e.g., methylphenidate, amphetamine, pemoline, phenelzine, protriptyline, gamma-hydroxybutyric acid, sodium oxybate, or other oxybate salts, modafinil, armodafinil, caffeine, and salts thereof, and combinations thereof, and the like, The compounds of the present invention may be administered in combination with compounds which are known in the art to be useful for preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, other orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-$NH_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activator receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579; (g) PPARδ agonists, such as those disclosed in WO97/28149; (h) PPAR cc/6 agonists, such as muraglitazar, and the compounds disclosed in U.S. Pat. No. 6,414, 002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001, 836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,N1e14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/1(364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide, (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373, 003, 5,387,595, 5,459,270, 5,494,926, 5,496,833, and 5,637, 699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors, such as verubecestat; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H$_3$ antagonists; AMPA agonists; PDE IV inhibitors; GABA$_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, (33 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, orexin receptor antagonists, such as suvorexant, other orexin agonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptable salts thereof.

In another embodiment, the subject compound may be employed in combination with an agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (S SRI); halogenated amphetamine derivatives, including chlorphentermine, cloforex, clortermine, dexfenfluramine, fenfluramine, picilorex and sibutramine; and pharmaceutically acceptable salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; Boc: tert-butyloxy carbonyl; BSA: bovine serum albumin; CbzCl: benzylchloroformate; CDI: carbonyl diimidazole; DCM (CH$_2$Cl$_2$): dichloromethane; DCE: dichloroethane; DEAD: diethylazodicarboxylate; DIPEA: N,N-diisopropylethylamine; DMF: N,N-dimethylformamide; DMSO: dimethylsulfoxide; EDC: N-(3-Dimethylaminopropyl)-N'-ethylcarbodiimide; Et$_3$N: triethylamine; EtOAc: ethyl acetate; EtOH: ethanol; HATU: 1-[Bis(dimethylamino)methylene]-1H-1,2,3-triazolo[4,5-b]pyridinium 3-oxid hexafluorophosphate aka. N-[(Dimethylamino)-1H-1,2,3-triazolo-[4,5-b]pyridin-1-ylmethylene]-N-methyl-methanaminium hexafluorophosphate N-oxide; HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; MeOH: methanol; MgSO$_4$: magnesium sulfate; Ms: methanesulfonyl; MTBE: methyl tert-butyl ether; NaHCO$_3$: sodium bicarbonate; NaOH: sodium hydroxide; NMM: N-methylmorpholine; PtO$_2$: platinum oxide; PyClu: 1-(chloro-1-pyrrolidinylmethylene)-pyrrolidinium hexafluorophosphate; rt: room temperature; SOCl$_2$: thionyl chloride; T3P: 2,4,6-tripropyl-1,3,5,2,4,6-trioxatriphosphorinane-2,4,6-trioxide; THF: tetrahydrofuran; TFA: trifluoracetic acid; X-Phos: 2-(dicyclohexyl-phosphino)-2',4',6'-triisopropylbiphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediate A (CIS)-4-phenylcyclohexanol

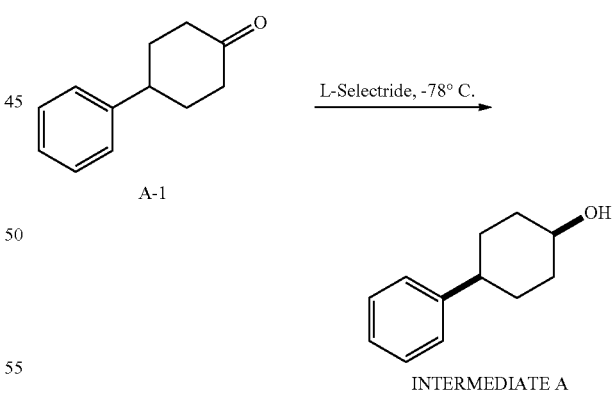

INTERMEDIATE A

To a mixture of 4-phenylcyclohexanone (A-1) (10.50 g, 60.3 mmol) in THF (201 ml) at −78° C. was added L-Selectride (102 ml, 102 mmol) in THF over 20 min. The mixture stirred at −78° C. for 3 hours before warming to 0° C. and stirring for an additional 2 hours. The reaction was quenched with a saturated solution of NH$_4$Cl (200 mL), extracted with EtOAc (250 mL×3), dried over Na$_2$SO$_4$, and concentrated. The residue was purified by column chromatography on silica (2% to 60% EtOAc/hexanes) to afford the title compound. MS: 199.9 (M+23).

Intermediate B

((CIS)-4-(chloromethoxy)cyclohexyl)benzene

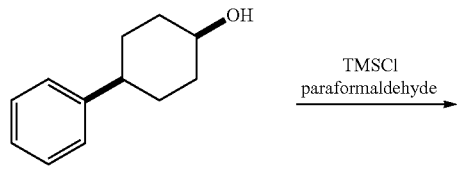

INTERMEDIATE A

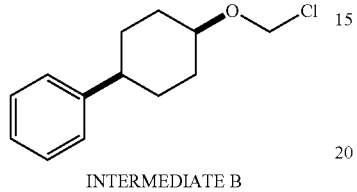

INTERMEDIATE B

To a mixture of (CIS)-4-phenylcyclohexanol (INTERMEDIATE A) (5.00 g, 28.4 mmol) in DCM (28.4 ml) at ambient temperature was added paraformaldehyde (0.937 g, 31.2 mmol) followed by the dropwise addition of TMS-Cl (10.88 ml, 85 mmol). The mixture stirred for 2 hours before concentrating, taking up in DCM (50 mL), drying over $Na_2SO_4$, and reconcentrating, and then placed under vacuum. The resulting residue was used directly without any further purification.

Intermediate C benzyl (CIS)-3-amino-2-((((CIS)-4-phenylcyclohexyl)oxy)methyl)pyrrolidine-1-carboxylate LDA, DMPU, −78° C.

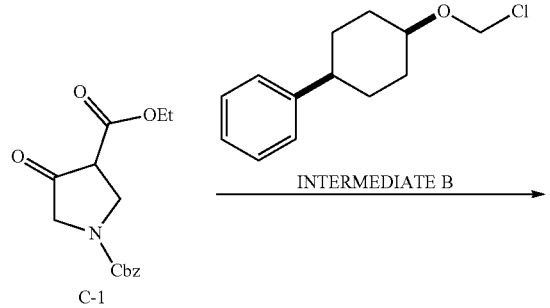

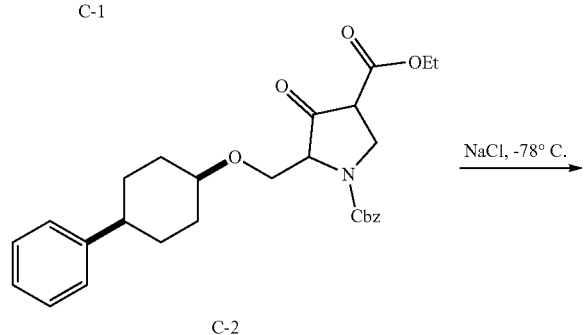

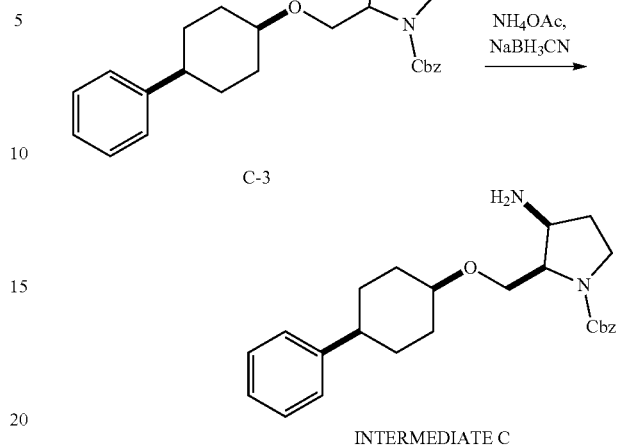

Step 1: 1-benzyl 3-ethyl 4-oxo-5-((((CIS)-4-phenylcyclohexyl)oxy)methyl)pyrrolidine-1,3-dicarboxylate (C-2)

To a mixture of 1-benzyl 3-ethyl 4-oxopyrrolidine-1,3-dicarboxylate (C-1) (7.50 g, 25.7 mmol) in THF (129 ml)/DMPU (12.42 ml, 103 mmol) at −78° C. was added LDA (28.3 ml, 56.6 mmol) in THF dropwise. The mixture was stirred for 15 min before adding ((CIS)-4-(chloromethoxy)-cyclohexyl)benzene (INTERMEDIATE B) (6.36 g, 28.3 mmol) in THF (15 mL). The mixture was stirred for another 20 min before quenching with a saturated solution of $NH_4Cl$ (100 mL). The mixture was warmed to ambient temperature, extracted with EtOAc (3×@ 200 mL), dried over $Na_2SO_4$, and concentrated. The residue was purified by column chromatography on silica (2% to 100% EtOAc/hexanes) to afford the title compound. MS: 480.5 (M+1).

Step 2: benzyl 3-oxo-2-((((CIS)-4-phenylcyclohexyl)oxy)methyl)pyrrolidine-1-carboxylate (C-3)

To a mixture of 1-benzyl 3-ethyl 4-oxo-5-((((CIS)-4-phenylcyclohexyl)oxy)-methyl)pyrrolidine-1,3-dicarboxylate (C-2) (4.00 g, 8.34 mmol) in DMSO (25.3 ml) was added sodium chloride (0.975 g, 16.68 mmol) and $H_2O$ (3.01 ml, 167 mmol). The mixture was heated to 130° C. and stirred for 2 hours before cooling to ambient temperature. The mixture was purified directly by column chromatography on C18 (5-95% MeCN/water with 0.05% TFA modifier) to afford the title compound. MS: 408.5 (M+1).

Step 3: benzyl (CIS)-3-amino-2-((((CIS)-4-phenylcyclohexyl)oxy)methyl)pyrrolidine-1-carboxylate (INTERMEDIATE C)

To a mixture of benzyl 3-oxo-2-(q(CIS)-4-phenylcyclohexyl)oxy)methyl)-pyrrolidine-1-carboxylate (C-3) (6.00 g, 14.72 mmol) in methanol (294 ml)) at ambient temperature was added ammonium acetate (34.0 g, 442 mmol). The mixture was stirred for 1 hour. $NaCNBH_4$ (0.925 g, 14.72 mmol) was added to the mixture for 16 more hours before it was concentrated. It was taken up in DCM (250 mL) and basified with a saturated solution of $NaHCO_3$ (250 mL).

Extract with DCM (3×@250 mL), dried over Na$_2$SO$_4$, and concentrated. The resulting residue was purified by column chromatography on C18 (5-95% MeCN/water with 0.05% TFA modifier) to afford the title compound. MS: 409.5 (M+1).

Intermediate D

N-((CIS)-2-(((((CIS)-4-phenylcyclohexyl)oxy)methyl)pyrrolidin-3-yl)methanesulfonamide

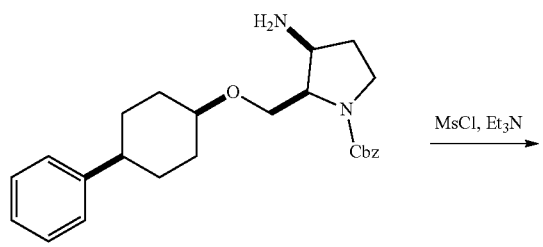

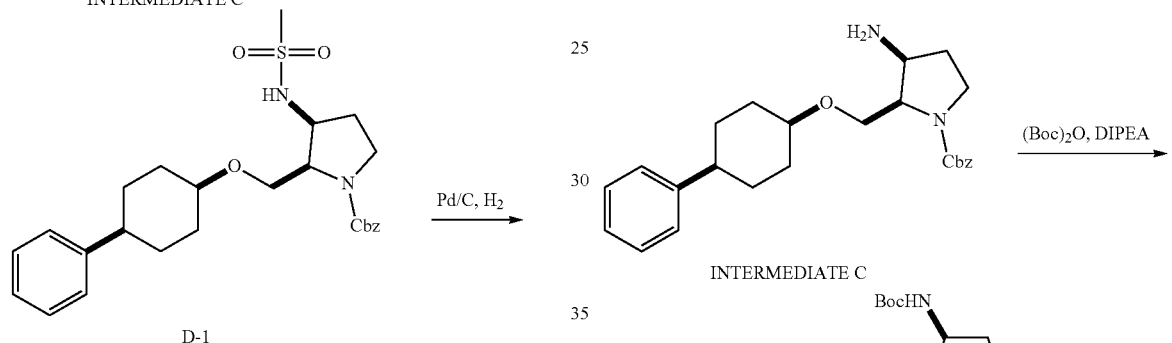

Step 1: benzyl (CIS)-3-(methylsulfonamido)-2-(((((CIS)-4-phenylcyclohexyl)oxy)methyl)-pyrrolidine-1-carboxylate (D-1)

To a mixture of benzyl 3-amino-2-(((((CIS)-4-phenylcyclohexyl)oxy)methyl)pyrrolidine-1-carboxylate (INTERMEDIATE C) (1.00 g, 2.448 mmol) in DCM (12.24 ml) at ambient temperature was added triethylamine (0.682 ml, 4.90 mmol) and methanesulfonyl chloride (0.229 ml, 2.94 mmol). The mixture was stirred for 2 hours before quenching with a saturated solution of NaHCO$_3$(25 mL). The mixture was extracted with EtOAc (3×@ 25 mL), dried over Na$_2$SO$_4$, and concentrated. The residue was purified by column chromatography on silica (5% to 70% 3:1 EtOAc: EtOH/hexanes) to afford the title compound. MS: 487.4 (M+1).

Step 2: N-((CIS)-2-(((((CIS)-4-phenylcyclohexyl)oxy)methyl)pyrrolidin-3-yl)methanesulfonamide (INTERMEDIATE D)

To a mixture of benzyl (CIS)-3-(methylsulfonamido)-2-(((((CIS)-4-phenylcyclohexyl)-oxy)methyl)pyrrolidine-1-carboxylate (D-1) (756 mg, 1.554 mmol) in MeOH (10.400 mL) at ambient temperature was added Pd/C (165 mg, 0.155 mmol). A balloon of H$_2$ was added (vacuum purge 3×) and the mixture stirred for 2 hours. The resulting mixture was filtered through a pad of diatomaceous earth and the filtrate was concentrated to afford the title compound. MS: 353.3 (M+1).

Intermediate E methyl (CIS)-3-amino-2-(((((CIS)-4-phenylcyclohexyl)oxy)methyl)pyrrolidine-1-carboxylate

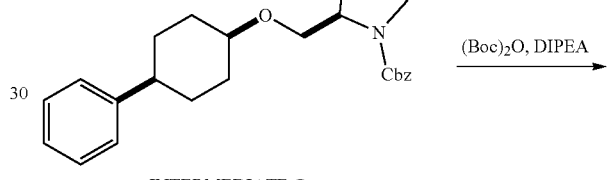

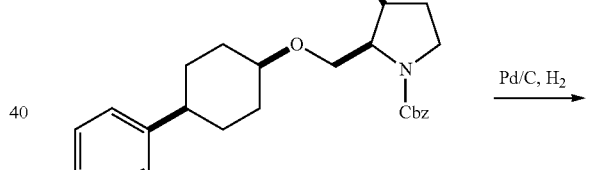

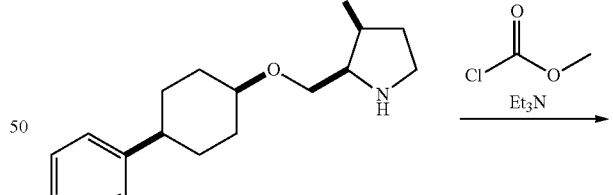

-continued

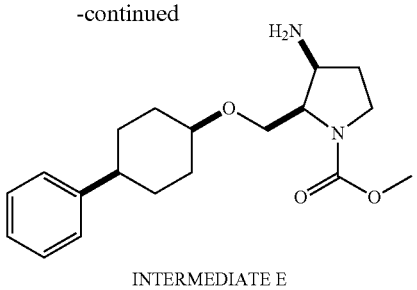

INTERMEDIATE E

Step 1: benzyl (CIS)-3-((tert-butoxycarbonyl) amino)-2-(((((CIS)-4-phenylcyclohexyl)oxy)-methyl)-pyrrolidine-1-carboxylate (E-1)

Di-tert-butyl dicarbonate (1042 mg, 4.78 mmol) was added to a stirred mixture of benzyl (CIS)-3-amino-2-(((((CIS)-4-phenylcyclohexyl)oxy)methyl)pyrrolidine-1-carboxylate (INTERMEDIATE C) (499.2 mg, 0.955 mmol) and DIEA (0.834 ml, 4.78 mmol) in THF (10 ml) and the mixture was stirred at room temperature for overnight. Hydrochloric acid (1M, 80 mL) was added and the mixture was extracted with ethyl acetate (3×80 mL). The combined organic fractions were washed with brine (saturated, 50 mL), dried ($Na_2SO_4$), filtered and the solvent was evaporated under reduced pressure. The residue was purified by column chromatography on silica gel (EtOAc:EtOH3:1/hexane 0-30%) to afford the title compound. MS: 510.5 (M+1).

Step 2: tert-butyl ((CIS)-2-(((((CIS)-4-phenylcyclohexyl)oxy)methyl)pyrrolidin-3-yl)carbamate (E-2)

Pd/C (48.1 mg, 0.452 mmol) was added to a stirred mixture of benzyl (CIS)-3-((tert-butoxycarbonyl)amino)-2-(((((CIS)-4-phenylcyclohexyl)oxy)methyl)pyrrolidine-1-carboxylate (E-1) (460 mg, 0.904 mmol) in MeOH (5 ml) and the mixture was stirred at room temperature for 2 h under a hydrogen atmosphere. The solution was filtered through diatomaceous earth, concentrated, dried to afford the title compound. MS: 375.8 (M+1).

Step 3: methyl (CIS)-3-((tert-butoxycarbonyl) amino)-2-(((((CIS)-4-phenylcyclohexyl)oxy)-methyl)-pyrrolidine-1-carboxylate (E-3)

Et3N (0.614 ml, 4.41 mmol) followed by methyl chloroformate (0.090 ml, 1.322 mmol) was added to a stirred mixture of tert-butyl ((CIS)-2-(((((CIS)-4-phenylcyclohexyl)oxy)-methyl)pyrrolidin-3-yl)carbamate (E-2) (330 mg, 0.881 mmol) in DCM (2 ml) and the mixture was stirred at room temperature for 5 min. It was concentrated, redissolved in MeOH (5 ml), and filtered, then the solution was purified by preparative HPLC Reverse phase C18 (Acetonitrile/Water+0.1% TFA) to afford the title compound. MS: 433.8 (M+1).

Step 4: methyl (CIS)-3-amino-2-(((((CIS)-4-phenylcyclohexyl)oxy)methyl)pyrrolidine-1-carboxylate (INTERMEDIATE E)

TFA (0.5 ml, 6.49 mmol) was added to a stirred mixture of methyl (CIS)-3-((tert-butoxycarbonyl)amino)-2-(((((CIS)-4-phenylcyclohexyl)oxy)methyl)pyrrolidine-1-carboxylate (E-3) (279 mg, 0.645 mmol) in DCM (10 ml) and the mixture was stirred at room temperature for 2 h. It was concentrated and dried to afford the title compound. MS: 333.3 (M+1).

Intermediates F and G

Benzyl (2S,3R)-3-amino-2-(((((CIS)-4-phenylcyclohexyl)oxy)methyl)pyrrolidine-1-carboxylate and
Benzyl (2R,3S)-3-amino-2-(((((CIS)-4-phenylcyclohexyl)oxy)methyl)pyrrolidine-1-carboxylate

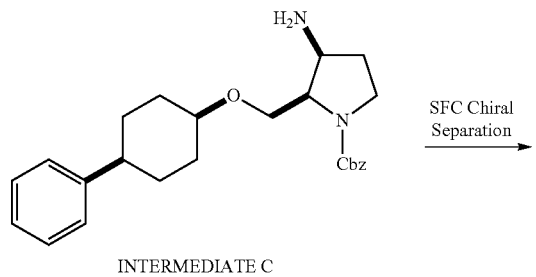

INTERMEDIATE C

SFC Chiral Separation →

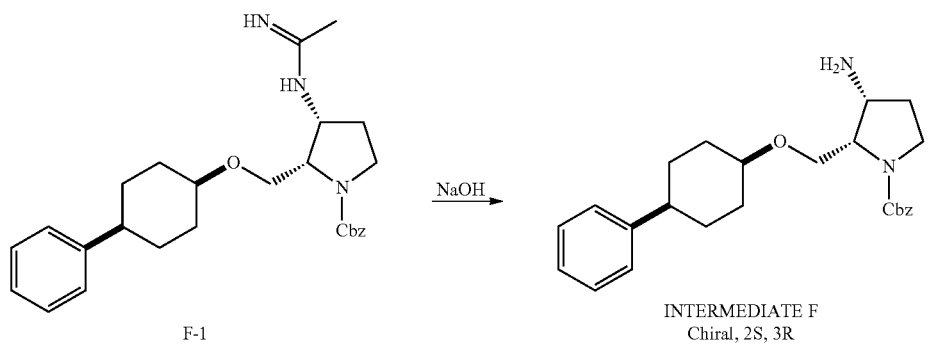

F-1

NaOH →

INTERMEDIATE F
Chiral, 2S, 3R

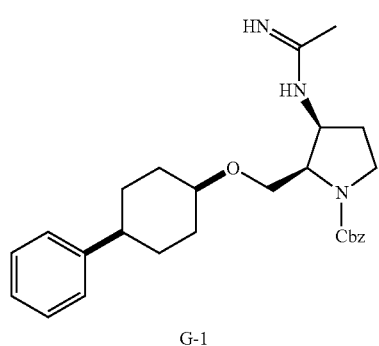

G-1

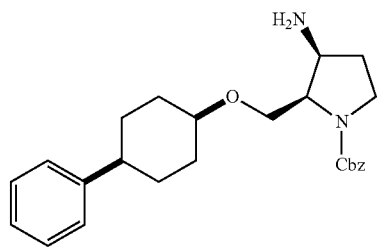

INTERMEDIATE G
Chiral, 2R, 3S

Step 1: benzyl (2 S,3R)-3-acetimidamido-2-((((CIS)-4-phenylcyclohexyl)oxy)methyl)pyrrolidine-1-carboxylate (F-1) and benzyl (2R,3S)-3-acetimidamido-2-((((CIS)-4-phenylcyclohexyl)oxy)methyl)pyrrolidine-1-carboxylate (G-1)

The mixture of benzyl (CIS)-3-amino-2-((((CIS)-4-phenylcyclohexyl)oxy)methyl)-pyrrolidine-1-carboxylate (INTERMEDIATE C) was subjected to SFC purification, using AD-H, 50×250 mm column, 25% (MeOH/ACN 1:1+0.2% DIPA), to obtain two chiral isomers: benzyl (2 S,3R)-3-acetimidamido-2-((((CIS)-4-phenylcyclohexyl)oxy)methyl)pyrrolidine-1-carboxylate (F-1, peak 1): MS: 450.3 (M+1); and benzyl (2R,3S)-3-acetimidamido-2-((((CIS)-4-phenylcyclohexyl)oxy)methyl)-pyrrolidine-1-carboxylate (G-1, peak 2): MS: 450.3 (M+1).

Step 2: benzyl (2R,3S)-3-amino-2-((((CIS)-4-phenylcyclohexyl)oxy)methyl)pyrrolidine-1-carboxylate (INTERMEDIATE G)

NaOH (2 ml, 2.000 mmol) was added to a stirred mixture of benzyl (2R,3S)-3-acetimidamido-2-((((CIS)-4-phenylcyclohexyl)oxy)methyl)pyrrolidine-1-carboxylate (G-1) (320 mg, 0.712 mmol) in Ethanol (2 ml) and the mixture was stirred at 80° C. for 4 h. The solution was concentrated, redissolved in MeOH (6 mL), and filtered. The residue was purified by preparative HPLC C-18 (Acetonitrile/Water+ 0.1% TFA) to afford the title compound. MS: 409.3 (M+1).

Intermediate H tert-butyl (2R,3S)-2-((4-isopropylphenoxy)methyl)-3-(methylsulfonamido)pyrrolidine-1-carboxylate

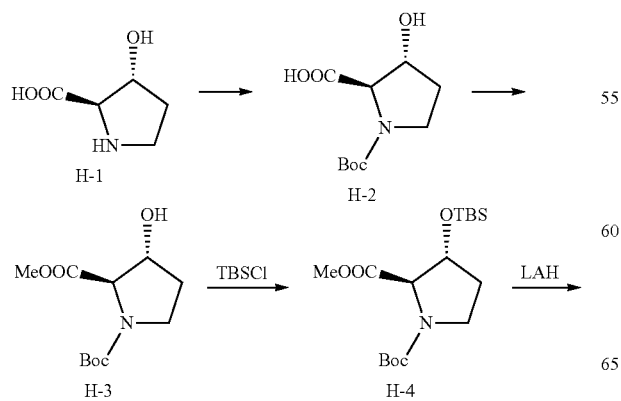

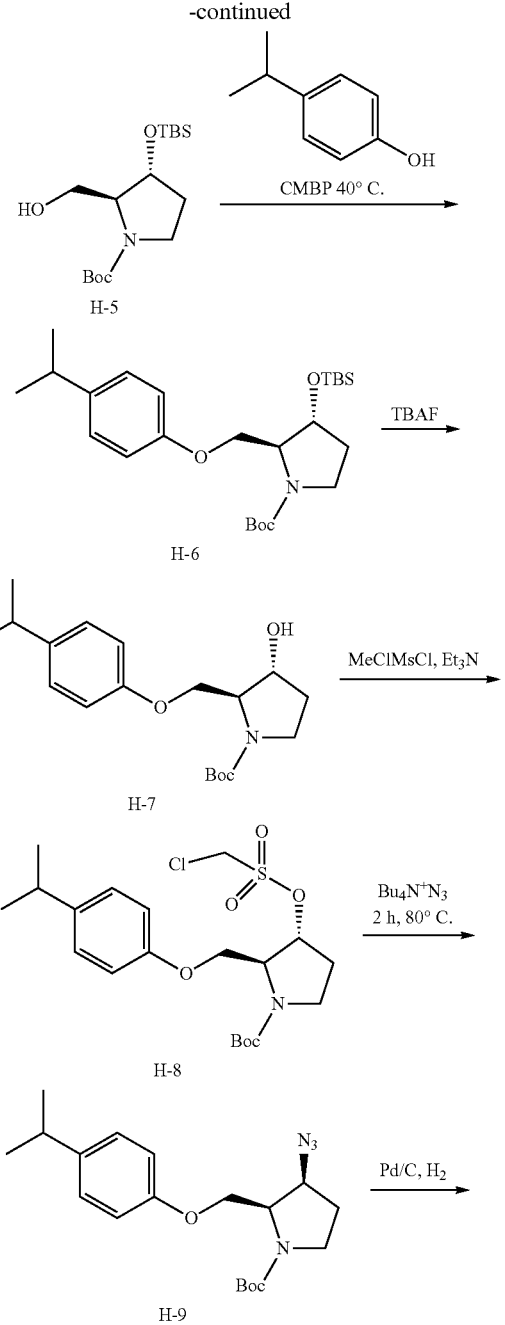

-continued

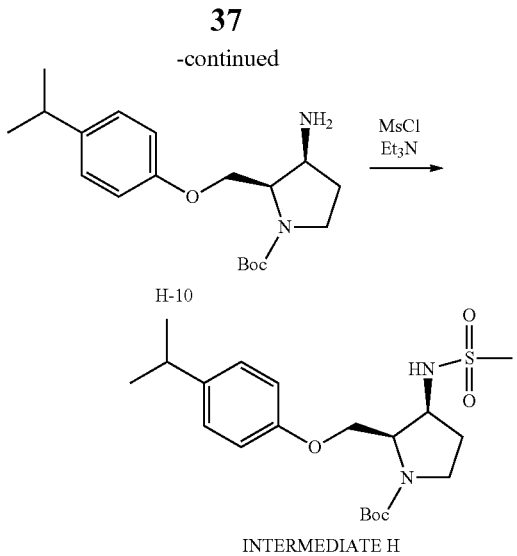

INTERMEDIATE H

Step 1: (2R,3R)-1-(tert-butoxycarbonyl)-3-hydroxy-pyrrolidine-2-carboxylic acid (H-2)

To a mixture of (2R,3R)-3-hydroxypyrrolidine-2-carboxylic acid (H-1) (516 mg, 3.94 mmol) in DCM (6 ml)/MeOH (1.200 ml) was added Et3N (1.207 ml, 8.66 mmol) and di-tert-butyl dicarbonate (1031 mg, 4.72 mmol). The resulting mixture was stirred at room temperature for overnight. The solvent was removed under vacuum to afford the title compound. MS: 231.0 (M+1).

Step 2: (2R,3R)-1-tert-butyl 2-methyl 3-hydroxy-pyrrolidine-1,2-dicarboxylate (H-3)

To a solution of (2R,3R)-1-(tert-butoxycarbonyl)-3-hydroxypyrrolidine-2-carboxylic acid (H-2)_(1.087 g, 4.7 mmol) in DCM (5 ml)/MeOH (5.00 ml) at 0° C. was slowly added (TRIMETHYLSILYL)DIAZOMETHANE (4.70 ml, 9.40 mmol). The solvent was removed under vacuum, and the residue was purified by chromatography column on silica gel (0-60% 3:1 EtOAc:EtOH/hexanes) to afford the title compound. MS: 268.1 (M+23).

Step 3: (2R,3R)-1-tert-butyl 2-methyl 3-((tert-butyldimethylsilyl)oxy)pyrrolidine-1,2-dicarboxylate (H-4)

To a mixture of (2R,3R)-1-tert-butyl 2-methyl 3-hydroxy-pyrrolidine-1,2-dicarboxylate (H-3) (370 mg, 1.509 mmol) in DMF (3 ml) was added 4-dimethylaminopyridine (212 mg, 1.735 mmol) and tert-butyldimethylsilyl chloride (261 mg, 1.735 mmol). The resulting mixture was stirred at room temperature for overnight. The reaction was quenched with EtOAc (20 ml), and washed with water and brine. The organic layer was dried over $MgSO_4$, filtered and concentrated to remove the solvent, the residue was purified by chromatography column on silica gel (0-30% 3:1 EtOAc:EtOH/hexanes) to afford the title compound. MS: 360.0 (M+1).

Step 4: (2S,3R)-tert-butyl 3-((tert-butyldimethylsilyl)oxy)-2-(hydroxymethyl)pyrrolidine-1-carboxylate (H-5)

To a mixture of (2R,3R)-1-tert-butyl 2-methyl 3-((tert-butyldimethylsilyl)oxy)-pyrrolidine-1,2-dicarboxylate (H-4) (420 mg, 1.168 mmol) in THF (6 ml) at −15° C. was added 1 M LiAlH4 (1.752 ml, 1.752 mmol) in THF. The reaction was stirred at −15° C. for 30 mins. The reaction was quenched with saturated NH4C1, and stirred for 5 mins. The mixture was extracted with EtOAC (3×10 ml). The combined organic was dried over MgSO4, filtered and concentrated, the residue was purified by chromatography column on silica gel (0-60% 3:1 EtOAc:EtOH/hexanes) to afford the title compound. MS: 332.0 (M+1).

Step 5: (2S,3R)-tert-butyl 3-((tert-butyldimethylsilyl)oxy)-2-((4-isopropylphenoxy)methyl)-pyrrolidine-1-carboxylate (H-6)

To a mixture of benzyl (2S,3R)-tert-butyl 3-((tert-butyldimethylsilyl)oxy)-2-(hydroxymethyl)pyrrolidine-1-carboxylate (H-5) (183 mg, 0.552 mmol) in Toluene (3 ml) was added 4-isopropylphenol (150 mg, 1.104 mmol) and 1M cyanomethylene-tributyl-phosphorane (1.104 ml, 1.104 mmol) in toluene. The resulting mixture was heated at 40° C. for weekend. It was quenched with EtOAc (10 ml), washed with water (10 ml), and the layers were separated. The organic layer was dried with MgSO4, filtered and concentrated, and the residue was purified by chromatography column on silica gel (0-60% 3:1 EtOAc:EtOH/hexanes) to afford the title compound. MS: 450.2 (M+1).

Step 6: (2S,3R)-tert-butyl 3-hydroxy-2-((4-isopropylphenoxy)methyl)pyrrolidine-1-carboxylate (H-7)

To a mixture of (2S,3R)-tert-butyl 3-((tert-butyldimethylsilyl)oxy)-2-((4-isopropyl-phenoxy)methyl)pyrrolidine-1-carboxylate (H-6) (224 mg, 0.498 mmol) in THF (2 ml) was added 1M TBAF (0.648 ml, 0.648 mmol) in THF. The reaction mixture was stirred at room temperature for overnight. The reaction mixture was concentrated to remove the solvent, and the residue was purified by chromatography column on silica gel (0-60% 3:1 EtOAc:EtOH/hexanes) to afford the title compound. MS: 336.0 (M+1).

Step 7: ((2S,3R)-tert-butyl 3-(((chloromethyl)sulfonyl)oxy)-2-((4-isopropylphenoxy)methyl)-pyrrolidine-1-carboxylate (H-8)

To a mixture of (2S,3R)-tert-butyl 3-hydroxy-2-((4-isopropylphenoxy)methyl)-pyrrolidine-1-carboxylate (H-7) (115 mg, 0.343 mmol) in DCM (3 ml) at 0° C. was added 2,6-lutidine (0.120 ml, 1.029 mmol) and chloromethanesulfonyl chloride (0.069 ml, 0.686 mmol). Then the reaction mixture was stirred in an ice bath for 20 mins and room temperature 30 mins. The reaction mixture was concentrated to remove the solvent, and the residue was purified by chromatography column on silica gel (0-20% 3:1 EtOAc:EtOH/hexanes) to afford the title compound. MS: 448.0 (M+1).

Step 8: (2R,3S)-tert-butyl 3-azido-2-((4-isopropylphenoxy)methyl)pyrrolidine-1-carboxylate(H-9)

To a mixture of (2S,3R)-tert-butyl 3-(((chloromethyl)sulfonyl)oxy)-2-((4-isopropylphenoxy)methyl)pyrrolidine-1-carboxylate (H-8) (150 mg, 0.335 mmol) in DMF (2 ml) was added tetrabutylammonium azide (476 mg, 1.674 mmol). The reaction mixture was heated at 80° C. for 2 h. The reaction was quenched with water (5 mL), and extracted with ether (2×3 mL). The combined organic was dried over MgSO4, filtered and concentrated. The residue was purified by chromatography column on silica gel (0-20% 3:1 EtOAc:EtOH/hexanes) to afford the title compound. MS: 361.0 (M+1).

Step 9: (2R,3S)-tert-butyl 3-amino-2-((4-isopropylphenoxy)methyl)pyrrolidine-1-carboxylate (H-10)

To a mixture of (2R,3S)-tert-butyl 3-azido-2-((4-isopropylphenoxy)methyl)pyrrolidine-1-carboxylate H-9 (71 mg, 0.197 mmol) in MeOH (1.5 ml) was added Pd—C(20.96 mg, 0.020 mmol). The mixture was degassed and filled with H2 twice. The reaction was stirred at room temperature under H₂ balloon for overnight, filtered through diatomaceous earth, and the diatomaceous earth was washed with MeOH. Concentrated the filtrate under reduced pressure to afford the title compound. MS: 335.1 (M+1).

Step 10: (2R,3S)-tert-butyl 2-((4-isopropylphenoxy)methyl)-3-(methylsulfonamido)pyrrolidine-1-carboxylate (INTERMEDIATE H)

To a mixture of (2R,3S)-tert-butyl 3-amino-2-((4-isopropylphenoxy)methyl)-pyrrolidine-1-carboxylate H-10 (65 mg, 0.194 mmol) in CH2Cl2 (1.6 ml) at 0° C. was added Et3N (0.163 ml, 1.166 mmol) and Ms-Cl (0.030 ml, 0.389 mmol). The mixture was stirred at 0° C. for 1 h. The reaction was quenched with water (3 ml), then extracted with DCM (3×3 ml). The combined organics were dried over MgSO4, then filtered and concentrated to remove the solvent. The residue was purified by chromatography column on silica gel (0-30% 3:1 EtOAc:EtOH/hexanes) to give the title compound. MS: 413.0 (M+1).

EXAMPLE 1

(CIS)-N-ethyl-3-(methylsulfonamido)-2-((((CIS)-4-phenylcyclohexyl)oxy)methyl)pyrrolidine-1-carboxamide

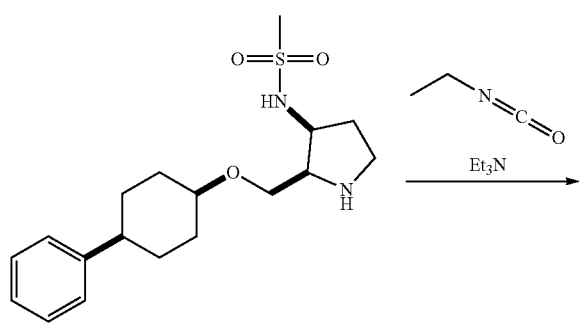

INTERMEDIATE D

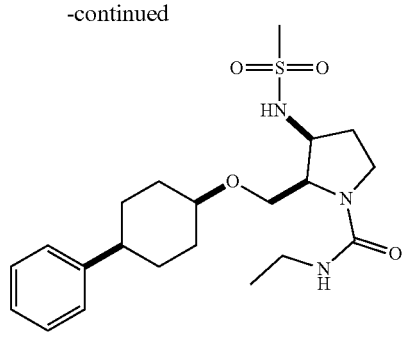

1

To a mixture of N-(((CIS)-2-(((((CIS)-4-phenylcyclohexyl)oxy)methyl)pyrrolidin-3-yl)methanesulfonamide (INTERMEDIATE D) (20 mg, 0.057 mmol) in DMF (378 μl) at ambient temperature was added triethylamine (23.73 μl, 0.170 mmol) and ethyl isocyanate (6.74 μl, 0.085 mmol). The resulting mixture was stirred for 1 hour, then the mixture was purified directly by column chromatography on C18 (5-95% MeCN/water with 0.05% TFA modifier) to afford the title compound. MS: 424.4 (M+1). $^1$H NMR (400 MHz, DMSO-d6) δ 7.25 (t, J=7.5 Hz, 2H), 7.21-7.06 (m, 4H), 6.16 (brs, 1H), 3.93-3.80 (m, 3H), 3.72-3.64 (m, 1H), 3.56 (s, 1H), 3.46-3.37 (m, 1H), 3.30-3.15 (m, 2H), 3.05-2.98 (m, 2H), 2.96 (s, 3H), 2.12-1.97 (m, 2H), 1.96-1.86 (m, 2H), 1.65 (p, J=12.2 Hz, 2H), 1.55-1.37 (m, 4H), 0.96 (t, J=7.1 Hz, 3H).

The following compounds were prepared according to the general procedure provided in Example 1, and procedures herein, by substituting the appropriate alkyl carbonochloridate and sulfamoyl chloride. The starting materials are either prepared as described in the intermediates section, commercially available, or may be prepared from commercially available reagents using conventional reactions well known in the art.

| Example Number | Structure | Name | Exact Mass [M + H]⁺ |
|---|---|---|---|
| 2 | 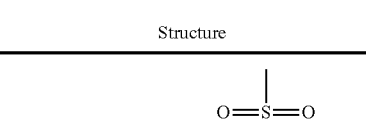 | methyl (CIS)-3-(methylsulfonamido)-2-((((CIS)-4-phenylcyclohexyl)oxy)-methyl)pyrrolidine-1-carboxylate | 411.3 |

-continued

| Example Number | Structure | Name | Exact Mass [M + H]+ |
|---|---|---|---|
| 3 | 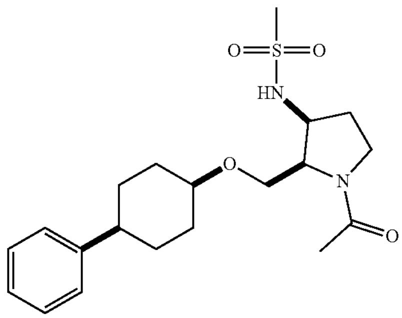 | N-((CIS)-1-acetyl-2-((((CIS)-4-phenylcyclohexyl)oxy)methyl)pyrrolidin-3-yl)methanesulfonamide | 395.3 |
| 4 | 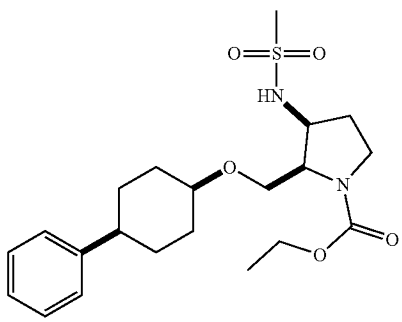 | ethyl (CIS)-3-(methylsulfonamido)-2-((((CIS)-4-phenylcyclohexyl)oxy)methyl)pyrrolidine-1-carboxylate | 425.3 |
| 5 | 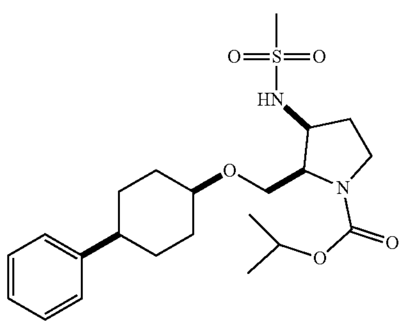 | isopropyl (CIS)-3-(methylsulfonamido)-2-((((CIS)-4-phenylcyclohexyl)oxy)methyl)pyrrolidine-1-carboxylate | 439.3 |
| 6 | 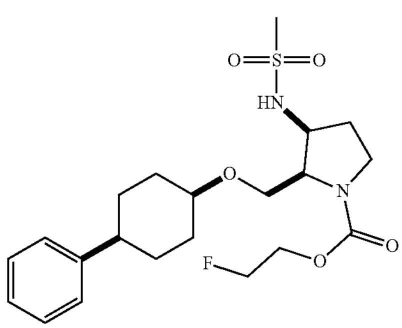 | 2-fluoroethyl (CIS)-3-(methylsulfonamido)-2-((((CIS)-4-phenylcyclohexyl)oxy)methyl)pyrrolidine-1-carboxylate | 443.3 |

-continued

| Example Number | Structure | Name | Exact Mass [M + H]⁺ |
|---|---|---|---|
| 7 | 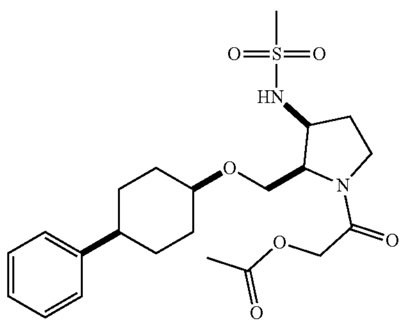 | 2-((CIS)-3-(methylsulfonamido)-2-(((((CIS)-4-phenylcyclohexyl)oxy)methyl)pyrrolidin-1-yl)-2-oxoethyl acetate | 453.3 |
| 8 | 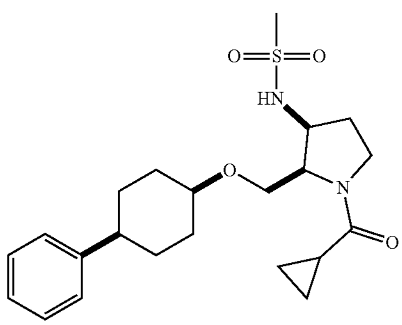 | N-((CIS)-1-(cyclopropanecarbonyl)-2-((((CIS)-4-phenylcyclohexyl)oxy)methyl)pyrrolidin-3-yl)methanesulfonamide | 421.3 |
| 9 | 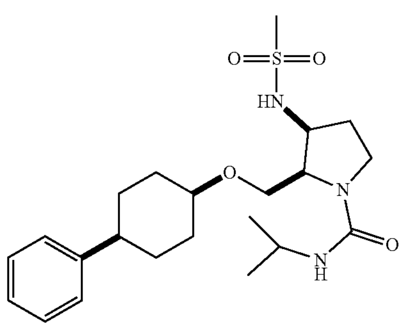 | (CIS)-N-isopropyl-3-(methylsulfonamido)-2-((((CIS)-4-phenylcyclohexyl)oxy)methyl)pyrrolidine-1-carboxamide | 438.4 |
| 10 | 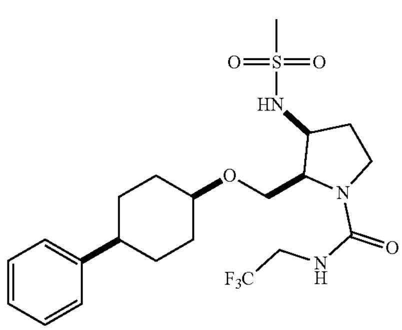 | (CIS)-3-(methylsulfonamido)-2-((((CIS)-4-phenylcyclohexyl)oxy)methyl)-N-(2,2,2-trifluoroethyl)pyrrolidine-1-carboxamide | 478.3 |

-continued

| Example Number | Structure | Name | Exact Mass [M + H]+ |
|---|---|---|---|
| 11 | 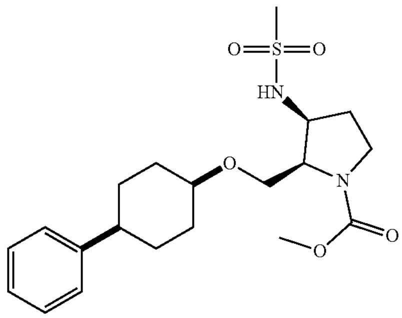 | methyl (2R,3S)-3-(methylsulfonamido)-2-(((((CIS)-4-phenylcyclohexyl)oxy)methyl)pyrrolidine-1-carboxylate | 411.3 |
| 12 | 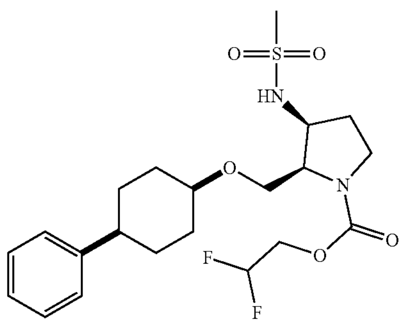 | 2,2-difluoroethyl (2R,3S)-3-(methylsulfonamido)-2-(((((CIS)-4-phenylcyclohexyl)oxy)methyl)pyrrolidine-1-carboxylate | 461.3 |

EXAMPLE 13 methyl (CIS)-3-(ethylsulfonamido)-2-(((((CIS)-4-phenylcyclohexyl)oxy)methyl)pyrrolidine-1-carboxylate

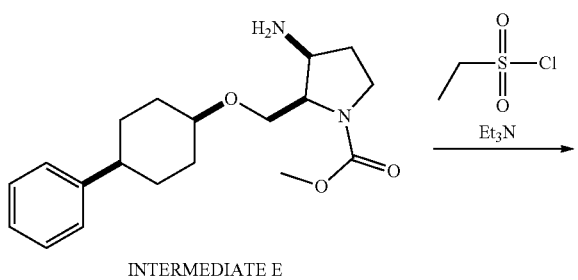

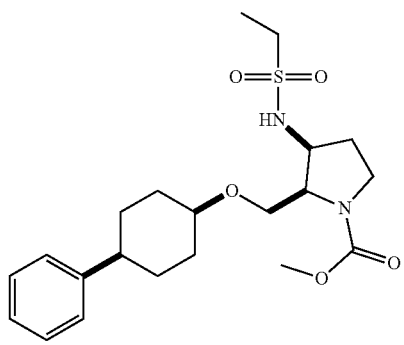

Et$_3$N (0.047 ml, 0.336 mmol) followed by ethanesulfonyl chloride (0.067 mmol) was added to a stirred mixture of (CIS)-3-amino-2-(((((CIS)-4-phenylcyclohexyl)oxy)-methyl)pyrrolidine-1-carboxylate (INTERMEDIATE E) (15 mg, 0.034 mmol), Et3N (0.047 ml, 0.336 mmol) in DCM (1 ml) and the mixture was stirred at room temperature for 30 min. The reaction mixture was concentrated, redissolved in MeOH (1 mL), and filtered. The solution was purified by preparative HPLC Reverse phase C-18 (Acetonitrile/Water+ 0.1% TFA) to afford the title compound. MS: 425.3 (M+1). $^1$H NMR (500 MHz, Methanol-d4) δ 7.35-7.09 (m, 5H), 4.12-3.97 (m, 2H), 3.97-3.77 (m, 1H), 3.77-3.63 (m, 5H), 3.57 (d, J=8.2 Hz, 1H), 3.51-3.38 (m, 1H), 3.16 (q, J=7.4 Hz, 2H), 2.56 (ddd, J=12.1, 8.8, 3.3 Hz, 1H), 2.26 (d, J=8.3 Hz, 2H), 2.13-2.02 (m, 2H), 2.02-1.43 (m, 6H), 1.37 (t, J=7.4 Hz, 3H).

The following compounds were prepared according to the general procedure provided in Examples 1 and 13, and procedures herein, by substituting the appropriate alkyl carbonochloridate and sulfamoyl chloride. The starting materials are either prepared as described in the intermediates section, commercially available, or may be prepared from commercially available reagents using conventional reactions well known in the art.

| Example Number | Structure | Name | Exact Mass [M + H]⁺ |
|---|---|---|---|
| 14 | 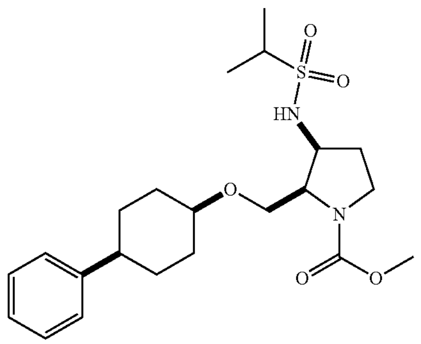 | methyl (CIS)-3-((1-methylethyl)sulfonamido)-2-(((((CIS)-4-phenylcyclohexyl)oxy)methyl)pyrrolidine-1-carboxylate | 439.3 |
| 15 | 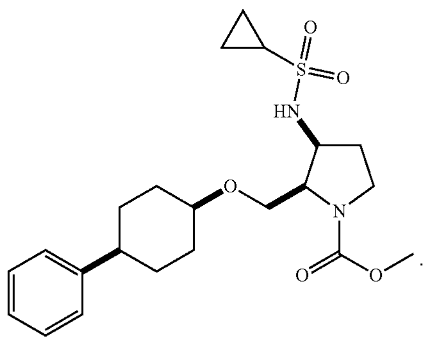 | methyl (CIS)-3-(cyclopropanesulfonamido)-2-(((((CIS)-4-phenylcyclohexyl)oxy)methyl)pyrrolidine-1-carboxylate | 437.3 |
| 16 | 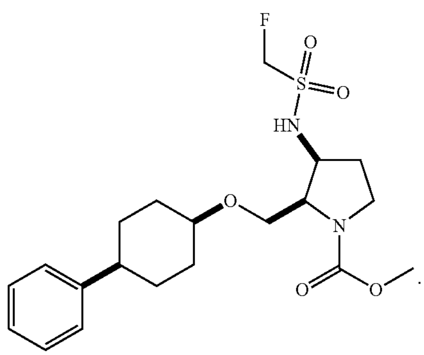 | methyl (CIS)-3-((fluoromethyl)sulfonamido)-2-(((((CIS)-4-phenylcyclohexyl)oxy)methyl)pyrrolidine-1-carboxylate | 429.2 |
| 17 | 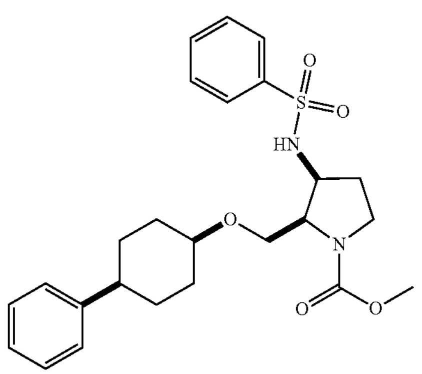 | methyl (CIS)-2-(((((CIS)-4-phenylcyclohexyl)oxy)methyl)-3-(phenylsulfonamido)pyrrolidine-1-carboxylate | 473.3 |

| Example Number | Structure | Name | Exact Mass [M + H]+ |
|---|---|---|---|
| 18 | 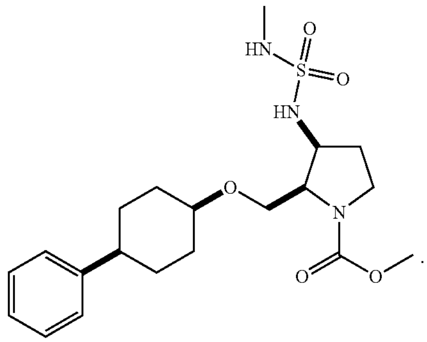 | methyl (CIS)-3-((N-methylsulfamoyl)amino)-2-(((((CIS)-4-phenylcyclohexyl)oxy)methyl)pyrrolidine-1-carboxylate | 426.3 |
| 19 | 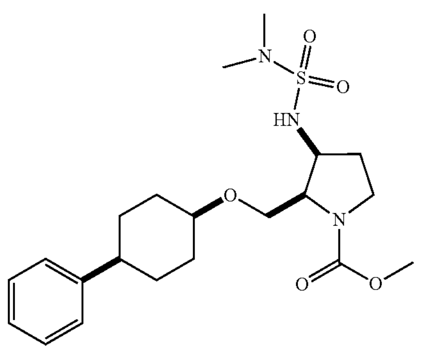 | methyl (CIS)-3-((N,N-dimethylsulfamoyl)amino)-2-(((((CIS)-4-phenylcyclohexyl)oxy)methyl)pyrrolidine-1-carboxylate | 440.3 |

EXAMPLE 20

N-((CIS)-2-(((((CIS)-4-phenylcyclohexyl)oxy)methyl)-1-(3,3,3-trifluoropropanoyl)pyrrolidin-3-yl)methanesulfonamide

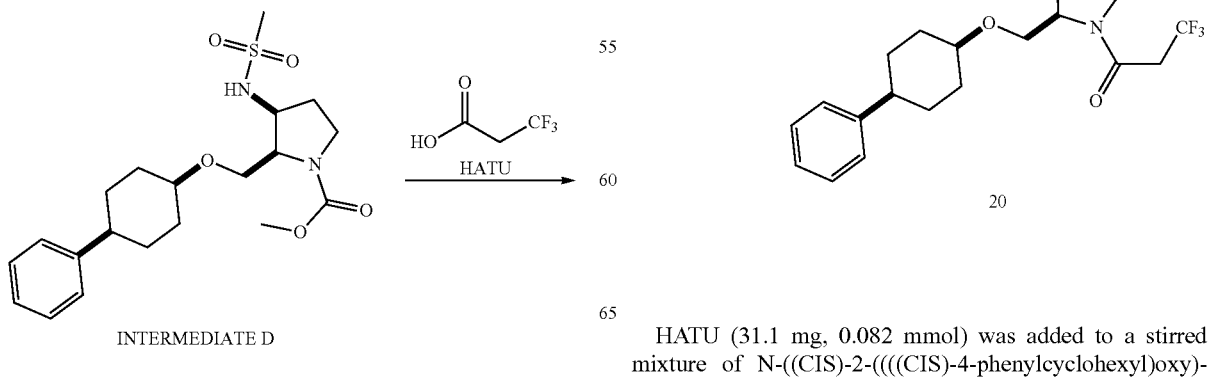

HATU (31.1 mg, 0.082 mmol) was added to a stirred mixture of N-((CIS)-2-(((((CIS)-4-phenylcyclohexyl)oxy)- methyl)pyrrolidin-3-yl)methanesulfonamide (INTERMEDIATE D) (14.4 mg, 0.041 mmol), 3,3,3-trifluoropropionic acid (10.46 mg, 0.082 mmol) and DIPEA (0.071 ml, 0.409 mmol) in DMF (1 ml) and the mixture was stirred at room temperature for 2 h. Following filtration, the solution was purified by preparative HPLC Reverse phase C18 (Acetonitrile/Water+0.1% TFA) to afford the title compound. MS: 463.3 (M+1). $^1$H NMR (500 MHz, Methanol-d4) δ 7.33-7.10 (m, 5H), 4.38-4.25 (m, 1H), 4.10 (ddt, J=11.7, 7.1, 3.9 Hz, 1H), 3.95-3.48 (m, 6H), 3.41 (qt, J=10.6, 5.2 Hz, 1H), 3.05 (d, J=5.0 Hz, 3H), 2.57 (ddt, J=12.0, 8.3, 3.4 Hz, 1H), 2.45-2.24 (m, 1H), 2.15-1.96 (m, 3H), 1.92-1.45 (m, 6H).

EXAMPLE 21

(CIS)-N-(cyclobutylmethyl)-3-(methylsulfonamido)-2-(((((CIS)-4-phenylcyclohexyl)oxy)-methyl)pyrrolidine-1-carboxamide

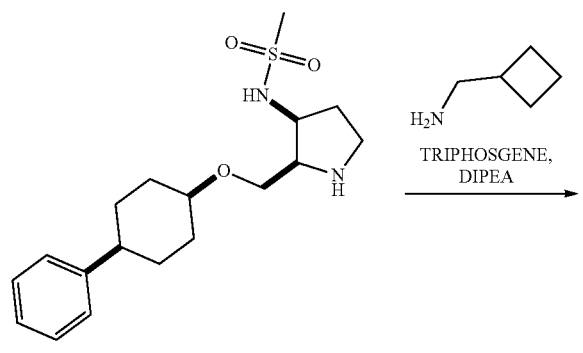

INTERMEDIATE D

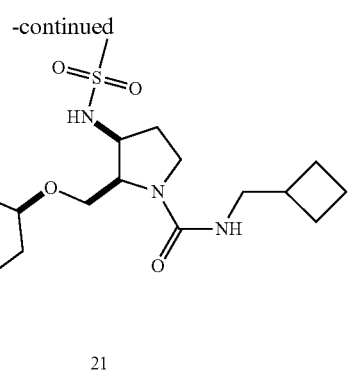

21

DIEA (0.037 ml, 0.211 mmol) followed by triphosgene (13.80 mg, 0.046 mmol) was added to a stirred mixture of N-((CIS)-2-(((((CIS)-4-phenylcyclohexyl)oxy)methyl)pyrrolidin-3-yl)methanesulfonamide (INTERMEDIATE D) (14.9 mg, 0.042 mmol) in DCM (1 ml) and the mixture was stirred at 0° C. for 15 min. A mixture of cyclobutylmethanamine (18.00 mg, 0.211 mmol), DIEA (0.037 ml, 0.211 mmol) in DCM (1.000 ml) was then added, and the reaction mixture was stirred at room temperature for Overnight. The reaction mixture was concentrated, redissolved in MeOH (1 ml) and filtered. The solution was purified by preparative HPLC Reverse phase C18 (Acetonitrile/Water+0.1% TFA) to afford the title compound. MS: 464.4 (M+1). $^1$H NMR (500 MHz, Methanol-d4) δ 7.33-7.08 (m, 5H), 4.06 (t, J=6.9 Hz, 2H), 3.89 (dd, J=9.8, 2.7 Hz, 1H), 3.67 (s, 1H), 3.65-3.57 (m, 1H), 3.53-3.37 (m, 2H), 3.25 (dd, J=13.4, 7.2 Hz, 1H), 3.13 (dd, J=13.4, 7.1 Hz, 1H), 3.04 (s, 3H), 2.64-2.41 (m, 2H), 2.33-2.12 (m, 2H), 2.12-1.93 (m, 4H), 1.93-1.47 (m, 10H).

The following compound was prepared according to the general procedure provided in Examples 1, 13, 20, 21, and procedures herein, by substituting the appropriate alkyl carbonochloridate and sulfamoyl chloride. The starting materials are either prepared as described in the intermediates section, commercially available, or may be prepared from commercially available reagents using conventional reactions well known in the art.

| Example Number | Structure | Name | Exact Mass [M + H]⁺ |
|---|---|---|---|
| 22 | 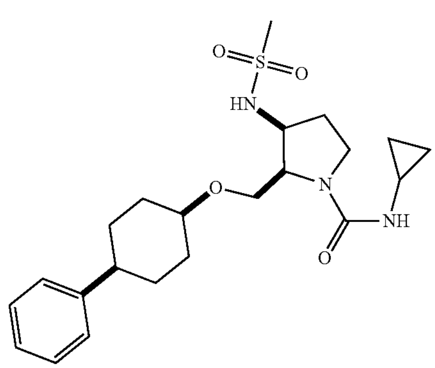 | (CIS)-N-cyclopropyl-3-(methylsulfonamido)-2-(((((CIS)-4-phenylcyclohexyl)oxy)methyl)pyrrolidine-1-carboxamide | 436.3 |

EXAMPLE 23

2,2-difluoroethyl (CIS)-3-(methylsulfonamido)-2-(((((CIS)-4-phenylcyclohexyl)oxy)methyl)-pyrrolidine-1-carboxylate

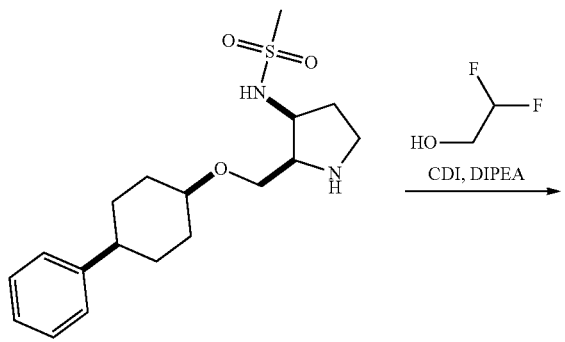

INTERMEDIATE D

DIEA (0.015 ml, 0.085 mmol) followed by CDI (72.0 mg, 0.444 mmol) was added to a stirred mixture of 2,2-difluoroethanol (42 mg, 0.512 mmol) in DCM (1 ml) and the mixture was stirred at room temperature for 5 min. To the reaction was then added the mixture of N-((CIS)-2-(((((CIS)-4-phenylcyclohexyl)oxy)methyl)pyrrolidin-3-yl)methanesulfonamide (INTERMEDIATE D) (14.9 mg, 0.042 mmol) and DIEA (0.015 ml, 0.085 mmol) in DCM (0.5 ml). The reaction mixture was stirred at room temperature for 1 h, concentrated, redissolved in MeOH (1 ml), and filtered. The solution was purified by preparative HPLC Reverse phase C18 (Acetonitrile/Water+0.1% TFA) to afford the title compound. MS: 461.3 (M+1). $^1$H NMR (500 MHz, Methanol-d4) δ 7.32-7.09 (m, 5H), 6.21-5.85 (m, 1H), 4.48-4.21 (m, 2H), 4.18-4.00 (m, 2H), 3.87 (ddd, J=33.8, 10.0, 3.4 Hz, 1H), 3.74 (t, J=9.6 Hz, 1H), 3.68-3.54 (m, 2H), 3.47 (dq, J=19.5, 9.2 Hz, 1H), 3.05 (s, 3H), 2.56 (t, J=12.2 Hz, 1H), 2.34-2.20 (m, 2H), 2.12-1.99 (m, 2H), 1.90-1.40 (m, 6H).

The following compound was prepared according to the general procedure provided in Examples 1, 13, 20, 21, and procedures herein, by substituting the appropriate alkyl carbonochloridate and sulfamoyl chloride. The starting materials are either prepared as described in the intermediates section, commercially available, or may be prepared from commercially available reagents using conventional reactions well known in the art.

| Example Number | Structure | Name | Exact Mass [M + H]$^+$ |
|---|---|---|---|
| 24 | 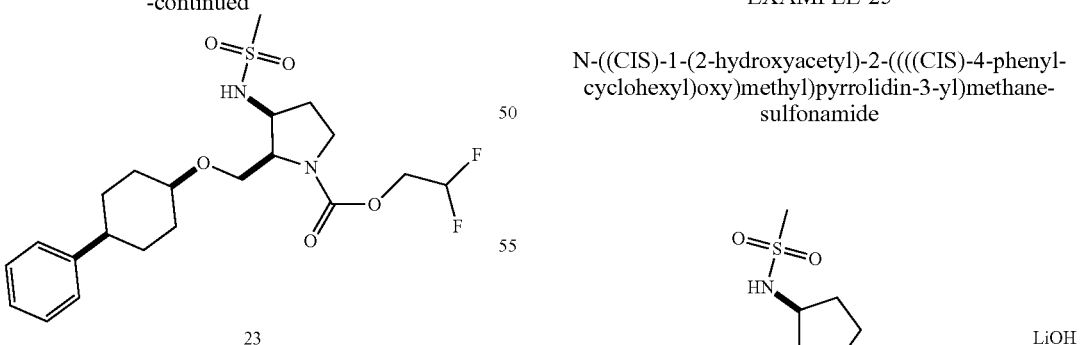 | 2,2,2-trifluoroethyl (CIS)-3-(methylsulfonamido)-2-(((((CIS)-4-phenylcyclohexyl)oxy)methyl)pyrrolidine-1-carboxylate | 479.3 |

EXAMPLE 25

N-((CIS)-1-(2-hydroxyacetyl)-2-(((((CIS)-4-phenylcyclohexyl)oxy)methyl)pyrrolidin-3-yl)methanesulfonamide

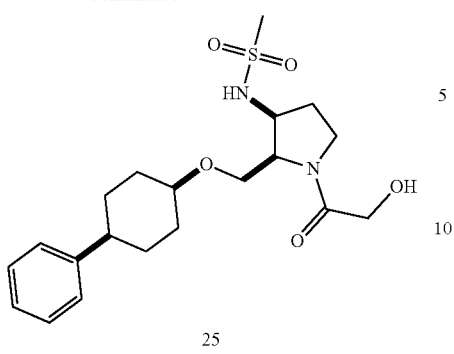

25

LiOH (1.323 mg, 0.055 mmol) was added to a stirred mixture of 2-(3-(methylsulfonamido)-2-(((((1s,4s)-4-phenylcyclohexyl)oxy)methyl)pyrrolidin-1-yl)-2-oxoethyl acetate (5001964-0134) (5 mg, 0.011 mmol) in Tetrahydrofuran (0.5 ml)/Water (0.500 ml) and the mixture was stirred at room temperature for 1 h, concentrated, redissolved in MeOH (1 ML), and filtered. The solution was purified by preparative HPLC Reverse phase C18 (Acetonitrile/Water+0.1% TFA) to afford the title compound. MS: 411.3 (M+1). $^1$H NMR (500 MHz, Methanol-d4) δ 7.33-7.10 (m, 5H), 4.31 (d, J=15.4 Hz, 1H), 4.26-4.18 (m, 1H), 4.17-4.01 (m, 2H), 3.94 (dd, J=10.0, 3.8 Hz, 1H), 3.77 (dd, J=10.1, 2.1 Hz, 1H), 3.70-3.52 (m, 3H), 3.52-3.43 (m, 1H), 3.05 (d, J=6.3 Hz, 3H), 2.56 (td, J=11.9, 3.4 Hz, 1H), 2.43-2.24 (m, 1H), 2.15-1.96 (m, 2H), 1.89-1.45 (m, 6H).

EXAMPLES 26 AND 27

N-((2S,3R)-1-(cyclopropanecarbonyl)-2-((((CIS)-4-phenylcyclohexyl)oxy)methyl)pyrrolidin-3-yl)methanesulfonamide and N-((2R,3S)-1-(cyclopropanecarbonyl)-2-((((CIS)-4-phenylcyclohexyl)oxy)methyl)pyrrolidin-3-yl)methanesulfonamide

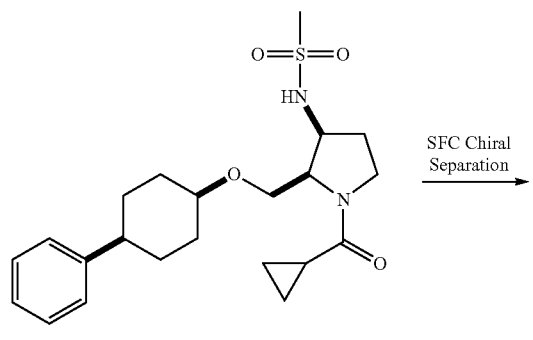

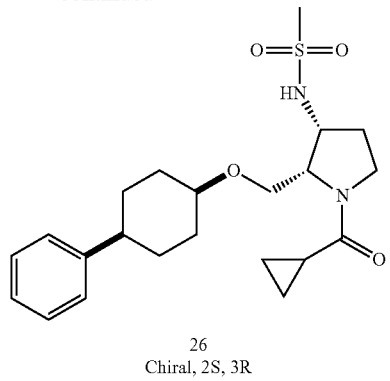

26
Chiral, 2S, 3R

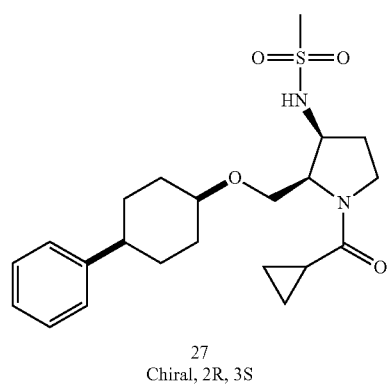

27
Chiral, 2R, 3S

The mixture of N-((CIS)-1-(cyclopropanecarbonyl)-2-((((CIS)-4-phenylcyclohexyl)-oxy)methyl)pyrrolidin-3-yl)methanesulfonamide (8) was subjected to SFC purification, OD-H, 21×250 mm, 25% (EtOH) to obtain two chiral isomers: N-((2S,3R)-1-(cyclopropanecarbonyl)-2-((((CIS)-4-phenylcyclohexyl)oxy)methyl)pyrrolidin-3-yl)methanesulfonamide (26, peak 1): MS: 421.3. $^1$H NMR (500 MHz, Methanol-d4) δ 7.34-7.05 (m, 5H), 4.52-4.21 (m, 1H), 4.13 (ddt, J=27.0, 11.3, 7.7 Hz, 1H), 3.99-3.85 (m, 1H), 3.84-3.43 (m, 4H), 3.06 (d, J=3.8 Hz, 3H), 2.56 (ddq, J=12.2, 8.3, 4.0 Hz, 1H), 2.48-1.97 (m, 4H), 1.92-1.38 (m, 7H), 1.04-0.72 (m, 4H); and N-((2R,3S)-1-(cyclopropanecarbonyl)-2-((((CIS)-4-phenylcyclohexyl)oxy)methyl)-pyrrolidin-3-1)methanesulfonamide (27, peak 2): MS: 421.3. $^1$H NMR (500 MHz, Methanol-d4) δ 7.35-7.08 (m, 5H), 4.52-4.21 (m, 1H), 4.13 (ddt, J=26.9, 11.2, 7.7 Hz, 1H), 3.99-3.85 (m, 1H), 3.83-3.47 (m, 4H), 3.06 (d, J=3.9 Hz, 3H), 2.56 (ddq, J=12.3, 8.3, 3.8 Hz, 1H), 2.47-1.97 (m, 4H), 1.89-1.38 (m, 7H), 1.03-0.72 (m, 4H).

EXAMPLE 28

(2R,3S)—N-ethyl-2-(((4-isopropyl cyclohexyl)oxy)methyl)-3-(methylsulfonamido)pyrrolidine-1-carboxamide

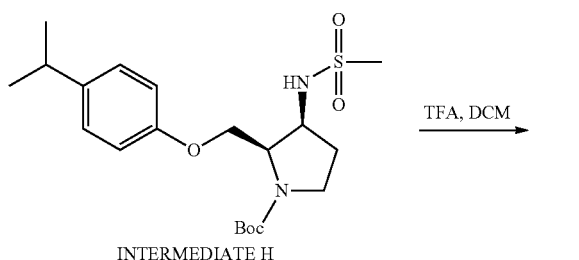

INTERMEDIATE H

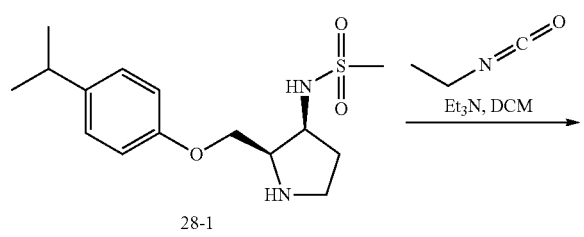

28-1

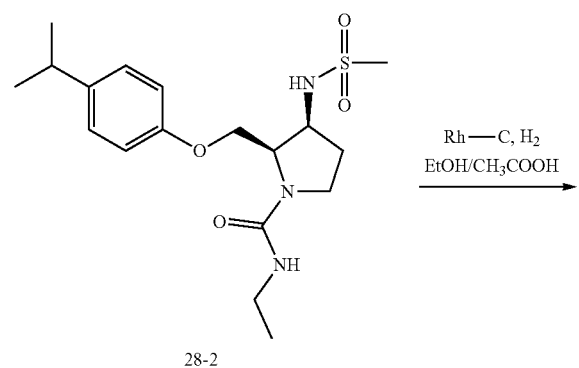

28-2

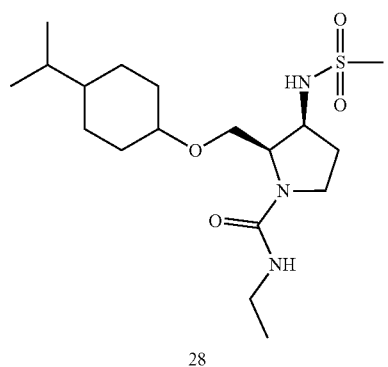

28

Step 1: N-((2R,3S)-2-((4-isopropylphenoxy)methyl)pyrrolidin-3-yl)methanesulfonamide (28-1)

To a mixture of tert-butyl (2R,3S)-2-((4-isopropylphenoxy)methyl)-3-(methylsulfonamido)pyrrolidine-1-carboxylate (INTERMEDIATE H) (65 mg, 0.158 mmol) in DCM (0.3 ml) was added TFA (0.121 ml, 1.576 mmol) at room temperature. The reaction was stirred at room temperature for 2 h, then concentrated to remove the solvent and afford the titled compound. MS: 313.0 (M+1).

Step 2: (2R,3S)—N-ethyl-2-((4-isopropylphenoxy)methyl)-3-(methyl sulfonamido)pyrrolidine-1-carboxamide (28-2)

To a mixture of N-((2R,3S)-2-((4-isopropylphenoxy)methyl)pyrrolidin-3-yl)methanesulfonamide (28-1) (21 mg, 0.049 mmol) in DCM (0.5 ml) was added Et3N (40 μl, 0.287 mmol) and ethyl isocyanate (10.5 mg, 0.148 mmol) at room temperature. The reaction mixture was stirred at room temperature for 2 h. The reaction was quenched with Water (3 ml), and extracted with DCM (3×3 ml). The combined organics were dried over MgSO4, filtered and concentrated to remove the solvent, and the residue was purified by chromatography column on silica gel (0-80% 3:1 EtOAc:EtOH/hexanes) to give the title compound. MS: 384.0 (M+1).

Step 3: (2R,3S)—N-ethyl-2-(((4-isopropylcyclohexyl)oxy)methyl)-3-(methylsulfonamido)pyrrolidine-1-carboxamide (28)

To a mixture of (2R,3S)—N-ethyl-2-(4-isopropylphenoxy)methyl)-3-(methylsulfonamido)-pyrrolidine-1-carboxamide (28-2) (17 mg, 0.044 mmol) in a mixture solvent of EtOH (1 ml)/Acetic Acid (0.111 ml) was added rhodium (1.838 μl, 0.222 mmol) on Carbon. The mixture was degassed and refilled with H2 twice. The reaction mixture was stirred at room temperature under $H_2$ for overnight, then filtered through diatomaceous earth, and washed with MeOH. It was concentrated, and to the residue was added saturated $NaHCO_3$ (10 ml) (to remove acetic acid), and extracted with DCM (3×10 ml). The combined organics were dried over MgSO4, filtered and concentrated to give the title compound. MS: 390.1 (M+1).

The following compounds were prepared according to the general procedure provided in Examples 1-4, and procedures herein, by substituting the appropriate alkyl carbonochloridate and sulfamoyl chloride. The starting materials are either prepared as described in the intermediates section, commercially available, or may be prepared from commercially available reagents using conventional reactions well known in the art.

| Example Number | Structure | Name | Exact Mass [M + H]⁺ |
|---|---|---|---|
| 29 | 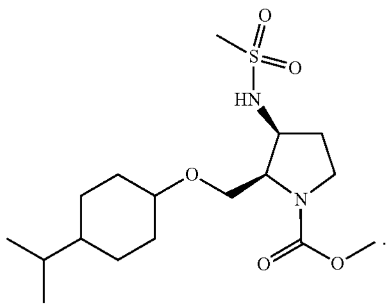 [SMILES: COC(=O)N1CC[C@H](NS(C)(=O)=O)[C@@H]1COC1CCC(C(C)C)CC1] | methyl (2R,3R)-2-(((4-isopropylcyclohexyl)oxy)methyl)-3-(methylsulfonamido)pyrrolidine-1-carboxylate | 377.0 |
| 30 | 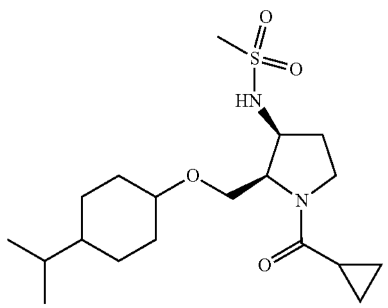 | N-((2R,3S)-1-(cyclopropanecarbonyl)-2-(((4-isopropylcyclohexyl)oxy)methyl)pyrrolidin-3-yl)methanesulfonamide | 387.1 |

The following table shows representative data for the compounds of the Examples as orexin receptor agonists as determined by the assays described herein.

| Example | OX2R Potency, EC50 (nM) | % Inhibition |
|---|---|---|
| 1 | 12 | 99.6% |
| 2 | 328 | 96.4% |
| 3 | 272 | 101.3% |
| 4 | 252 | 98.9% |
| 5 | 2630 | 92.8% |
| 6 | 216 | 98.4% |
| 7 | 361 | 98.8% |
| 8 | 77.9 | 101.6% |
| 9 | 36.4 | 99.2% |
| 10 | 3.65 | 103.7% |
| 11 | 115 | 100.2% |
| 12 | 81 | 101.1% |
| 13 | 136 | 99.9% |
| 14 | 372 | 101.3% |
| 15 | 299 | 99.8% |
| 16 | 177 | 100.7% |
| 17 | 3700 | 82.3% |
| 18 | 66.5 | 98.5% |
| 19 | 39.4 | 98.8% |
| 20 | 1010 | 96.4% |
| 21 | 5.65 | 103.2% |
| 22 | 250 | 99.6% |
| 23 | 59.6 | 101.3% |
| 24 | 493 | 100.2% |
| 25 | 361 | 103.3% |
| 26 | INACTIVE | 17.1% |
| 27 | 48.7 | 100.2% |
| 28 | 57.8 | 99.8% |
| 29 | 358 | 99.0% |
| 30 | 433 | 100.6% |

With respect to other compounds such as those disclosed in US 2017/0226137, WO 2017/135306, WO 2018/164191, WO 2018/164192, WO 2019/027003, WO 2019/027058 or U.S. Pat. No. 9,527,807, it would be desirable that the present compounds exhibit unexpected properties, such as equipotency among compounds wherein X is O and X is NH. For example, in contrast to compounds of US 2017/0226137, WO 2017/135306, WO 2018/164191, WO 2018/164192, WO 2019/027003, WO 2019/027058 or U.S. Pat. No. 9,527,807, the compounds of the present examples possess equipotency among the carbamate compounds wherein X is O and the urea compounds wherein X is NH.

As indicated by the data herein, the compounds of the present examples provide unexpected potency as orexin receptor agonists. The distinction in potency as orexin receptor agonists provides greater functional activity and potential for enhanced in vivo efficacy and may provide benefits over other orexin receptor agonists that are known in the art.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

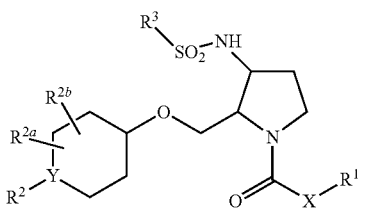

wherein:

X is —O— or —NH—, or X may be a direct bond to $R^1$;

Y is N or CH;

$R^1$ is selected from:
  (1) -$C_{1-6}$alkyl, where the alkyl is unsubstituted or substituted with one to six substituents independently selected from $R^4$, and
  (2) -$C_{3-6}$cycloalkyl, where the cycloalkyl is unsubstituted or substituted with one to six substituents independently selected from $R^4$;

$R^2$ is selected from:
  (1) hydrogen,
  (2) -$C_{1-6}$alkyl, where the alkyl is unsubstituted or substituted with one to six substituents independently selected from $R^4$,
  (3) -$C_{3-6}$cycloalkyl, where the cycloalkyl is unsubstituted or substituted with one to six substituents independently selected from $R^4$,
  (4) -phenyl, where the phenyl is unsubstituted or substituted with one to three substituents independently selected from $R^4$, and
  (5) -heteroaryl, where the heteroaryl is selected from: pyridyl, pyrimidinyl, and pyrazinyl, and the heteroaryl is unsubstituted or substituted with one to three substituents independently selected from $R^4$;

$R^{2a}$ and $R^{2b}$ are independently selected from:
  (1) hydrogen,
  (2) hydroxyl,
  (3) halogen, and
  (4) -$C_{1-6}$alkyl, where the alkyl is unsubstituted or substituted with one to six substituents independently selected from halogen;

$R^3$ is phenyl, where the phenyl is unsubstituted or substituted with one to three substituents independently selected from $R^4$, $R^4$ is selected from:
  (1) hydroxyl,
  (2) halogen,
  (3) $C^{1-6}$alkyl, which is unsubstituted or substituted with one to six fluoro,
  (4) -$C_{3-6}$cycloalkyl,
  (5) —O-$C_{1-6}$alkyl,
  (6) —O (C=O)-$C_{1-6}$ alkyl,
  (7) —$NH_2$,
  (8) —NH-$C_{1-6}$alkyl,
  (9) —$NO_2$,
  (10) phenyl,
  (11) —$CO_2H$, and
  (12) —CN;

or a pharmaceutically acceptable salt thereof.

2. The compound of claim 1 or a pharmaceutically acceptable salt thereof wherein X is —O—.

3. The compound of claim 1 or a pharmaceutically acceptable salt thereof wherein $R^1$ is selected from:
  (1) methyl,
  (2) ethyl,
  (3) —$CH_2OH$,
  (4) —$CH_2CF_3$,
  (5) —$CH_2CHF_2$,
  (6) —$CH(CH_3)_2$,
  (7) —$CH_2CH_2CH_2F$,
  (8) cyclopropyl,
  (9) —$CH_2$-cyclopropyl,
  (10) —$CH_2$-cyclobutyl, and
  (11) —$CH_2O(C=O)CH_3$.

4. The compound of claim 1 or a pharmaceutically acceptable salt thereof wherein $R^2$ is selected from:
  (1) hydrogen,
  (2) —$CH_2(CH_3)_2$,
  (3) —$CF_3$,
  (4) —$CH_2CHF_2$,
  (5) —$CH_2CF_3$, and
  (6) phenyl, which is unsubstituted or substituted with —$CF_3$ or —$CH_2CF_3$.

5. A compound which is selected from: methyl 2-(((4-phenylcyclohexyl)oxy)methyl)-3-(phenylsulfonamido)pyrrolidine-1-carboxylate; methyl (CIS)-2-((((CIS)-4-phenylcyclohexyl)oxy)methyl)-3-(phenylsulfonamido)pyrrolidine-1-carboxylate; or a pharmaceutically acceptable salt thereof.

6. A pharmaceutical composition which comprises an inert carrier and a compound of claim 1 or a pharmaceutically acceptable salt thereof.

* * * * *